United States Patent
McNern et al.

(10) Patent No.: US 12,016,765 B2
(45) Date of Patent: Jun. 25, 2024

(54) ESOPHAGEAL ATRESIA BRIDGE DEVICE AND METHODS OF TREATING ESOPHAGEAL ATRESIA

(71) Applicant: BOSTON SCIENTIFIC SCIMED, INC., Maple Grove, MN (US)

(72) Inventors: Louis McNern, Donegal (IE); Enda Connaughton, Galway (IE); Richard Crawford, Galway (IE); Gary Gilmartin, Foxford (IE); Matthew Montague, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 80 days.

(21) Appl. No.: 17/714,516

(22) Filed: Apr. 6, 2022

(65) Prior Publication Data

US 2022/0226098 A1 Jul. 21, 2022

Related U.S. Application Data

(63) Continuation of application No. 16/703,136, filed on Dec. 4, 2019, now Pat. No. 11,389,286.
(Continued)

(51) Int. Cl.
*A61F 2/04* (2013.01)
*A61B 17/11* (2006.01)
*A61F 2/93* (2013.01)

(52) U.S. Cl.
CPC .......... *A61F 2/04* (2013.01); *A61B 17/1114* (2013.01); *A61F 2/93* (2013.01); *A61F 2002/044* (2013.01)

(58) Field of Classification Search
CPC ........ A61F 2/04; A61F 2/93; A61F 2002/044; A61F 2220/0008; A61F 2220/0033;
(Continued)

(56) References Cited

U.S. PATENT DOCUMENTS

| 3,771,526 A | 11/1973 | Rudie |
| 5,454,365 A | 10/1995 | Bonutti |

(Continued)

FOREIGN PATENT DOCUMENTS

| WO | 2009100313 A1 | 8/2009 |
| WO | 2013126246 A1 | 8/2013 |
| WO | 2017202766 A1 | 1/2018 |

OTHER PUBLICATIONS

Damian et al; "Robotic Implant to Apply Tissue Traction Forces in the Treatment of Esophageal Atresia", 2014 IEEE International Convention on Robotics & Automation, 786-792, 2014.
(Continued)

*Primary Examiner* — Paul B Prebilic
(74) *Attorney, Agent, or Firm* — Seager, Tufte & Wickhem, LLP

(57) ABSTRACT

An esophageal atresia bridge device including a proximal anchor, a distal anchor, and a brace extending between the proximal anchor and the distal anchor. The brace permits the proximal anchor to move toward the distal anchor to apply a controlled tension that pulls the esophagus together and stretches the esophagus over time. A method of treating esophageal atresia may include inserting an elongate member of an esophageal atresia device into a mouth of a patient, the esophageal atresia device including a rotatable member including a threaded region, and rotating the rotatable member relative to the elongate member to longitudinally move the distal end of the elongate member relative to the rotatable member in order to apply a force to a proximal pouch of the patient's esophagus.

19 Claims, 39 Drawing Sheets

Related U.S. Application Data

(60) Provisional application No. 62/775,689, filed on Dec. 5, 2018.

(58) Field of Classification Search
CPC ...... A61F 2220/0041; A61F 2220/0025; A61F 2250/0007; A61F 2250/0008; A61F 2250/0039; A61F 2250/0065
See application file for complete search history.

(56) References Cited

U.S. PATENT DOCUMENTS

| | | | |
|---|---|---|---|
| 5,527,324 | A | 6/1996 | Krantz et al. |
| 5,755,772 | A | 5/1998 | Evans et al. |
| 6,126,686 | A | 10/2000 | Badylak et al. |
| 6,357,104 | B1 | 3/2002 | Myers |
| 6,626,936 | B2 | 9/2003 | Stinson |
| 7,101,392 | B2 | 9/2006 | Heath |
| 7,282,057 | B2 | 10/2007 | Surti et al. |
| 7,621,950 | B1 | 11/2009 | Globerman et al. |
| 7,938,852 | B2 | 5/2011 | Andreas et al. |
| 8,545,499 | B2 | 10/2013 | Lozier et al. |
| 8,579,958 | B2 | 11/2013 | Kusleika |
| 8,795,301 | B2 | 8/2014 | Burnett et al. |
| 9,168,041 | B2 | 10/2015 | Zaritsky et al. |
| 2005/0228412 | A1* | 10/2005 | Surti .................. A61B 17/1114 606/153 |
| 2007/0049954 | A1* | 3/2007 | Caty .................. A61B 17/1114 606/153 |
| 2008/0114466 | A1 | 5/2008 | Shelton |
| 2009/0012544 | A1 | 1/2009 | Thompson et al. |
| 2010/0286705 | A1 | 11/2010 | Vassiliades, Jr. |
| 2013/0226205 | A1 | 8/2013 | Zaritsky et al. |
| 2014/0277335 | A1 | 9/2014 | Greenberg et al. |
| 2016/0120638 | A1 | 5/2016 | Michalak |
| 2017/0311952 | A1 | 11/2017 | Potter, Jr. et al. |
| 2018/0228491 | A1 | 8/2018 | Potter, Jr. |
| 2019/0239887 | A1* | 8/2019 | Potter, Jr. ............. A61B 5/1076 |

OTHER PUBLICATIONS http://www.we-are-eat.org/innovative-care-managements/growth-induction-foker-procedure-esophageal-atresia/ accessed on Jan. 16, 2020.

https://www.cookmedical.com/newsroom/cook-medicals-flourish-receives-authorization-for-pediacatric-esophageal-atresia/ accessed on Jan. 16, 2020.

Oehlerking, et al; "A Hydraulically Controlled Nonoperative Magnetic Treatment for Long Gap Esophageal Atresia", J. Med. Devices 5 (2), 2011.

Tyberg et al; "Endoscopic Ultrasound-Guided Gastrojejunostomy with a Lumen-Apposing Metal Stent: A Mutlicenter, International Experience", Endoscopy International Open 2016; 04: E276-E281, 2016.

Chen et al; "EUS-Guided Gastroenterostomy is Comparable to Enteral Stenting with Fewer Re-Interventions in Malignant Gastic Outlet Obstruction," Surg Endosc. ()2017) 31:2946-2952, Nov. 10, 2016.

Ge et al; "EUS Guided Gastrojejunostomy with Lumen Apposing Metal Stent Placement for Palliation of Malignant Gastric Outlet Obstruction", Gastrointestinal Endoscopy vol. 87, No. 6S, Jun. 2018.

* cited by examiner

ESOPHAGEAL ATRESIA BRIDGE DEVICE AND METHODS OF TREATING ESOPHAGEAL ATRESIA

CROSS-REFERENCE TO RELATED APPLICATIONS

This application is a continuation of U.S. application Ser. No. 16/703,136, now U.S. Pat. No. 11,389,286, filed Dec. 4, 2019, which claims the benefit of U.S. Provisional Application No. 62/775,689 filed Dec. 5, 2018, the entire disclosure of which is hereby incorporated by reference.

TECHNICAL FIELD

The present disclosure pertains to medical devices, and methods for using medical devices. More particularly, the present disclosure pertains to esophageal atresia bridge devices.

BACKGROUND

Esophageal atresia is a condition where individuals are born with an incomplete esophagus which does not connect the throat to the stomach. There are several different types of esophageal atresia situations which makes it difficult for the current corrective procedures to be performed successfully. Moreover, the current procedures, for example the Fokker Process, is very invasive and causes individuals extreme trauma. In some cases, individuals are paralyzed and made unconscious for several weeks which causes weight loss and muscle wasting. The Fokker Process uses sutures which are attached to both pouch ends of the esophagus. The sutures are periodically pulled a small amount, allowing the esophagus to grow around 5 cm each time and stretch the esophagus over time. During that time, the individuals remain paralyzed and unconscious. Another shortcoming of this procedure is that the applied forces are uncontrolled and can leave the blood at the end of the esophagus unable to perfuse. As such, there is an ongoing need to provide alternative esophageal atresia bridge devices and procedures.

BRIEF SUMMARY

This disclosure provides design, material, and use alternatives for medical devices, including esophageal atresia bridge devices.

In a first example, an esophageal atresia bridge device may comprise a proximal anchor configured to anchor to a proximal section of an esophagus, a distal anchor configured to anchor to a distal section of the esophagus, and a brace configured to position the proximal anchor an initial distance from the distal anchor and thereafter, permit the proximal anchor to move toward the distal anchor to apply a controlled tension that pulls the proximal section of the esophagus towards the distal section of the esophagus and stretch the esophagus over time.

Alternatively or additionally to any of the examples above, in another example, the brace may be further configured to hold the proximal anchor and the distal anchor from moving toward and away from one another.

Alternatively or additionally to any of the examples above, in another example, the brace may comprise a ratchet mechanism to permit incremental advancement of the proximal anchor toward the distal anchor.

Alternatively or additionally to any of the examples above, in another example, the brace may comprise a screw mechanism to permit longitudinal advancement of the proximal anchor toward the distal anchor.

Alternatively or additionally to any of the examples above, in another example, the bridge device may comprise an expandable stent and a proximal flared region of the stent forms the proximal anchor and a distal flared region of the stent forms the distal anchor.

Alternatively or additionally to any of the examples above, in another example, the brace may comprise an intermediate portion of the stent between the proximal portion and the distal portion radially constrained by a sheath disposed along the intermediate portion of the stent.

Alternatively or additionally to any of the examples above, in another example, the sheath may include a crocheted filament configured to unravel to allow the intermediate portion to radially expand and axially contract, decreasing a distance between the proximal anchor and the distal anchor.

Alternatively or additionally to any of the examples above, in another example, the sheath may be configured to degrade over time to allow the intermediate portion to radially expand and axially contract, decreasing a distance between the proximal anchor and the distal anchor.

Alternatively or additionally to any of the examples above, in another example, the sheath may be configured to have a first portion of the sheath degrade faster than a second portion of the sheath.

In another example, an esophageal atresia bridge device may comprise a proximal anchor configured to anchor to a proximal section of an esophagus, a distal anchor configured to anchor to a distal section of the esophagus, and a link extending between the proximal anchor and the distal anchor. The link may be configured to position the proximal anchor at an initial first position from the distal anchor, permit the proximal anchor to move toward the distal anchor to a second position to apply a controlled tension that pulls the proximal section of the esophagus towards the distal section of the esophagus and stretch the esophagus over a first duration of time, and thereafter, further permit the proximal anchor to move further toward the distal anchor to a third position to apply a controlled tension that pulls the proximal section of the esophagus further towards the distal section of the esophagus and further stretch the esophagus over a second duration of time.

Alternatively or additionally to any of the examples above, in another example, the proximal anchor may comprise a flange and the distal anchor may comprise a fastener.

Alternatively or additionally to any of the examples above, in another example, the proximal anchor may comprise a first flange and the distal anchor may comprise a second flange.

Alternatively or additionally to any of the examples above, in another example, the bridge device may comprise an expandable stent and a proximal flared region of the stent forms the proximal anchor and a distal flared region of the stent forms the distal anchor and the link may comprise a radially constrained intermediate portion of the stent between the proximal portion and the distal portion, wherein radially expansion of the intermediate portion moves the proximal anchor toward the distal anchor.

Alternatively or additionally to any of the examples above, in another example, the link may comprise a ratchet mechanism to permit incremental advancement of the proximal anchor toward the distal anchor.

Alternatively or additionally to any of the examples above, in another example, the link may comprise a screw mechanism to permit longitudinal advancement of the proximal anchor toward the distal anchor.

In another example, an esophageal atresia bridge device may comprise an expandable stent including a proximal flared region configured to anchor to a proximal section of an esophagus, a distal flared region configured to anchor to a distal section of the esophagus, and an intermediate portion. The esophageal atresia bridge device may also comprise a sheath configured to radially constrain and axially elongate the intermediate portion.

Alternatively or additionally to any of the examples above, in another example, the sheath may include a set of removable sections and removing one or more of the removable sections allows the intermediate portion to radially expand and axially contract, decreasing a distance between the proximal flared region and the distal flared region.

Alternatively or additionally to any of the examples above, in another example, the sheath may be configured to degrade over time to allow the intermediate portion to radially expand and axially contract, decreasing a distance between the proximal flared region and the distal flared region.

Alternatively or additionally to any of the examples above, in another example, the sheath may include a first portion having a greater wall thickness than degrades second portion of the sheath.

Alternatively or additionally to any of the examples above, in another example, the sheath may be a crocheted filament configured to unravel to allow the intermediate portion to radially expand and axially contract, decreasing a distance between the proximal flared region and the distal flared region.

The above summary of some illustrative embodiments is not intended to describe each disclosed embodiment or every implementation of the present disclosure. The Figures and Description which follow more particularly exemplify these and other illustrative embodiments.

BRIEF DESCRIPTION OF THE DRAWINGS

The disclosure may be more completely understood in consideration of the following detailed description in connection with the accompanying drawings, in which.

Figure 1A:
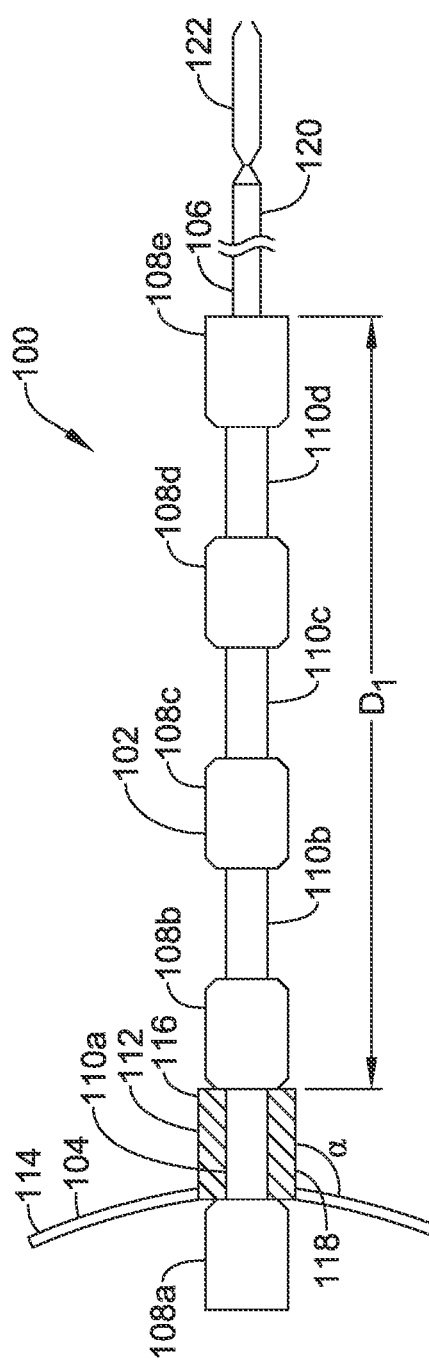
FIGS. 1A-1C illustrate an example of an esophageal atresia bridge device configured for emplacement in the esophagus of a patient.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

The current disclosure relates to esophageal atresia bridge devices. In some cases, the bridge device may comprise a proximal anchor, a distal anchor, and a brace or an elongate member configured to apply a controlled tension or force to the esophagus that pulls a proximal section or a proximal pouch of the esophagus towards a distal section or a distal pouch of the esophagus and stretches the esophagus over time. In some cases, the brace may be configured to hold the proximal anchor and the distal anchor from moving toward and away from one another. In some instances, the brace may be a ratchet mechanism that also permits incremental advancement of the proximal anchor towards the distal anchor. In other instances, the brace may be a screw mechanism that permits calibrated advancement of the proximal anchor towards the distal anchor. In some cases, the bridge device may be a metal stent and the brace may be a sheath configured to constrict an intermediate portion of the metal stent. In some instances, the sheath may be perforated into sections and the intermediate portion of the metal stent may radially expand and axially contract as a section of the perforated sheath is torn away to move the proximal anchor towards the distal anchor. In other instances, the sheath may be degradable and the intermediate portion of the metal stent may radially expand and axially contract as the sheath degrades over time to move the proximal anchor towards the distal anchor.

FIG. 1A illustrates an example of an esophageal atresia bridge device 100 configured for emplacement in the esophagus of a patient using methods of delivery described herein. As shown, the bridge device 100 may include a brace/link 102, a proximal anchor 104, and a distal anchor 106. The brace/link 102 extends from the proximal anchor 104 to the distal anchor 106, interconnecting the proximal anchor 104 to the distal anchor 106. In some cases, the brace 102 may be formed of any biocompatible material suitable for chronic implantation in a patient. Some examples include polymers such as soft thermoplastic materials, polyurethanes, silicone rubbers, nylon, polyethylenes, fluorinated hydrocarbon polymers, and the like. In some embodiments, the brace 102 may include a highly flexible material such as low density polyethylene (LDPE), polyvinylchloride, THV, etc. In some instances, the brace 102 may be formed from or comprise metal, for example, stainless steel, such as high tensile stainless steel, or other materials, including metals and metal alloys, such as tungsten, gold, titanium, silver, copper, platinum, palladium, iridium, ELGILOY nickel-cobalt alloys, cobalt chrome alloys, molybdenum tungsten alloys, tantalum alloys, titanium alloys, nickel-titanium alloys (e.g., nitinol), etc. The brace 102 may be formed from a lubricious polymer, such as a fluorocarbon (e.g., polytetrafluoroethylene (PTFE)), a polyamide (e.g., nylon), a polyolefin, a polyimide, or the like). Additional polymeric materials which may make up the brace 102 include polyethylene, polyvinyl chloride (PVC), ethyl vinyl acetate (EVA), polyethylene terephthalate (PET), and their mixtures and copolymers. Another useful class of polymers is thermoplastic elastomers, including those containing polyesters as components. For example, the brace 102 may be formed by extruding a rigid thermoplastic elastomer polymer.

The brace 102 may be colored to enhance surgical visibility by, for example, incorporating some amount of titanium dioxide. The brace may also be doped with or include a component made with a radiopaque material such as barium sulfate ($BaSO_4$), bismuth trioxide ($Bi_2O_3$), bismuth subcarbonate ($Bi_2O_2CO_3$), bismuth oxychloride (BiOCl), and tungsten. Still in further embodiments, the brace 102 may be composed of a combination of several these materials either as a mixture or as a series of layers or parts that are combined, molded, welded or otherwise joined together.

In some cases, the brace 102 may be configured to secure the proximal anchor 104 an initial distance ($D_1$) from the distal anchor 106 and thereafter, permit the proximal anchor 104 to move toward the distal anchor 106 to apply a controlled tension that pulls a proximal section of the esophagus of the patient towards a distal section of the esophagus of the patient and stretch the esophagus over time. In some instances, as shown in FIG. 1A, the brace 102 may include a ratchet mechanism that permits incremental advancement of the proximal anchor 104 towards the distal anchor 106. In some examples, the ratchet mechanism may include a plurality of detents, such as a plurality of recesses 108A-108E and elevations 110A-110D configured to hold the proximal anchor 104 and the distal anchor 106 from moving toward and away from one another at a plurality of discrete positions. In some examples, the inclusion of a plurality of detents, such as several recesses 108A-108E, offers a wider range of position options for the proximal anchor 104 relative to the distal anchor 106 that allows for a wider range of incremental tension/force magnitudes for pulling the proximal section of the esophagus to the distal section of the esophagus of the patient. It is expected that a physician may choose which detent to use based on the needs of the patient. In some cases, the recesses 108A-108E may have widths larger than the proximal anchor 104. In this configuration, the proximal anchor 104 may be allowed to move along or oscillate along the recess it is currently placed. As such, the elevations 110A-110D may still be configured to hold the proximal anchor 104 at its current recess location. However, the ability to move along the recess may allow the brace 102 to apply a controlled tension or force that can vary slightly to accommodate fluctuations in the tissue of an esophagus and potentially avoid tearing of the tissue.

According to various embodiments, the proximal anchor 104 may comprise a collar 112 defining a lumen and a securing mechanism(s) 114 configured to push against and engage tissue of the patient when the bridge device 100 is implanted inside the proximal section of the esophagus of the patient. In some cases, the securing mechanism(s) 114 may be flanges, flaps, tines, hooks, fans, or a combination thereof, etc. that are formed as a single-piece, with the collar 112 by a molding and/or cutting process. In other instances, the securing mechanism(s) 114 may be flanges, flaps, tines, hooks, fans, or a combination thereof, etc. that are formed of multiple components. In some cases, the securing mechanism(s) 114 may have an end attached to the collar 112 in any suitable manner, which may include mechanical structures such as hinges, screws, pins and/or any other suitable fastener, or bonding such as through the use of a medical adhesive. Heat shrink tubing may be placed over the end of the securing mechanism(s) 114 for securing to the collar 112, or laser, sonic, heat, or other welding process may be used to attach the end of the securing mechanism(s) 114 for securing to the collar 112.

In some examples, the securing mechanism 114 may include several fingers, arms, or other projections that are radially spaced from one another around the collar 112. For example, the fingers or arms of the securing mechanism 114 may be symmetrically located around the collar 112. In some cases, the fingers or arms of the securing mechanisms 114 may be limited to one side of the collar 112. In some instances, as shown, the securing mechanism 114 may include a continuous flange or rim of material fully surrounding the collar 112. In some examples, the securing mechanisms may each be similar in design/structure, or, in other examples, the width, length, shape, or other features of the securing mechanisms may vary from one another.

In some examples, the securing mechanism(s) 114 may be attached to or configured relative to the collar 112 such that the securing mechanism(s) 114 has a desired degree of angular separation (α), with the central axis of the lumen of the collar 112. For example, in some cases, the securing mechanism(s) 114 may be configured so that there is a 45° angle between the securing mechanism(s) 114 and the central axis of the lumen of the collar 112 in a relaxed, non-compressed state. In some cases, the angle of separation a may be 15°, 30°, 60°, 90°, etc. In some cases, the securing mechanism(s) may be configured to move, retract, or compress towards the central axis of the lumen of the collar 112 to a compressed state by applying force thereto, such as during implantation or delivery of the bridge device 100. In some cases, the securing mechanism(s) 114 may be configured to move, swing, or extend away from the central axis of the lumen of the collar 112, or otherwise revert from the compressed state to a non-compressed state, as shown, such as during deployment of the bridge device 100, for example.

The proximal anchor 104 may be made of any biocompatible material to allow for chronic implantation in a patient. For example, any of the materials discussed above with regard to the brace 102 may be used. In some examples, the proximal anchor 104 may be made of the same material as the brace 102. In other examples, the proximal anchor 104 may be comprised of different materials than the brace 102. In certain embodiments, the securing mechanism(s) 114 may be comprised of a different, stiffer, material than the collar 112. Alternatively, the securing mechanism(s) 114 may be softer than the collar 112. According to various embodiments, multiple durometers may be used with the proximal anchor 104. In some cases, the securing mechanism(s) 114 may be formed over a wire which may extend to or terminate short of the end of the securing mechanism(s) 114. In some examples the securing mechanism(s) 114 may be formed of silicone while a different polymer of stiffer or harder character is used for the collar 112. In other examples, the securing mechanism(s) may be coated or uncoated nitinol or other metal, making them generally stiffer than the lumen. In some cases, the proximal anchor 104 may be radiopaque.

In an example, a diameter of the lumen of the collar 112 of the proximal anchor 104 may be equal to or slightly less than an outer diameter of the recesses 110A-110D of the ratchet mechanism. The lumen of the collar 112 may have a single diameter or, in other examples, the lumen of the collar 112 may have a diameter that varies along the length of the proximal anchor 104. In some examples, the diameter of the lumen of the collar 112 may be largest at an open proximal end 116, may taper along the length of the lumen of the collar 112, and may be smallest at an open distal end 118. This may be beneficial for allowing the proximal anchor 104 to more easily fit around and be placed onto the ratchet mechanism. However, this is not necessary. In some examples the collar 112 may be radially stretchable or elastic to allow the diameter of the lumen of the collar 112 to expand to allow passage over the elevations 108A-108E of the ratchet mechanism through the lumen of the collar 112.

According to various embodiments, the distal anchor 106 may include an elongate shaft, such as a hollow tube 120, and a fastener 122 positioned at a distal end of the elongate shaft (e.g., the hollow tube 120). For clarity, the fastener 122 has been enlarged in FIGS. 1A-1C In some cases, during implantation of the bridge device 102, the bridge device 102 may be connected to a delivery device (not shown) operated by an individual/physician. In some examples, the delivery device may have a handle assembly equipped with a trigger that, when pulled, actuates the fastener 122 via a lever-and-spring system, a pull wire, or other actuator, for example, within the hollow tube 120. In the example shown in FIG. 1A, the fastener 122 may be a clamping mechanism having distal ends configured to grip or grasp a wall of the distal section of the esophagus. In other instances, the fastener 122 may be configured to penetrate through the wall of the distal section of the esophagus to engage the fastener 122 with the wall of the distal section of the esophagus. In other examples, the fastener 122 may be a hook, pin, screw latch, clip, or any mechanism configured engage the wall of the distal section of the esophagus to anchor the bridge device 102 to the distal section of the esophagus. In some cases, the fastener 122 may be initially open and close when actuated, such as when the trigger is pulled. Moreover, the handle assembly may also have a locking mechanism configured to lock the fastener 122 closed to keep the bridge device 102 anchored to the distal section of the esophagus. Variations on the basic form of the distal anchor 106 (e.g., the hollow tube 120 and the fastener 122) may be implemented depending on the needs/preferences of the patient and physician and variations can be made in the length and weight of the distal anchor 106. Additionally, the distal anchor 106 may be made of any biocompatible material to allow for chronic implantation in a patient, such as any of the materials discussed above with regard to the brace 102 or the proximal anchor 104 and in various embodiments, the hollow tube 102 and the fastener 122 may be comprised of the same or different materials.

Figure 1B:
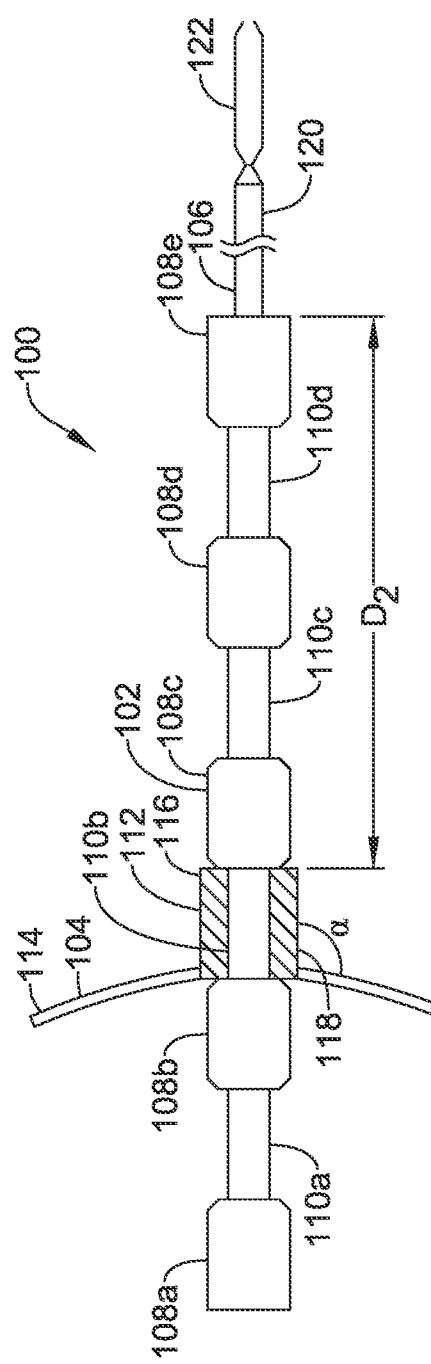
Figure 1C:
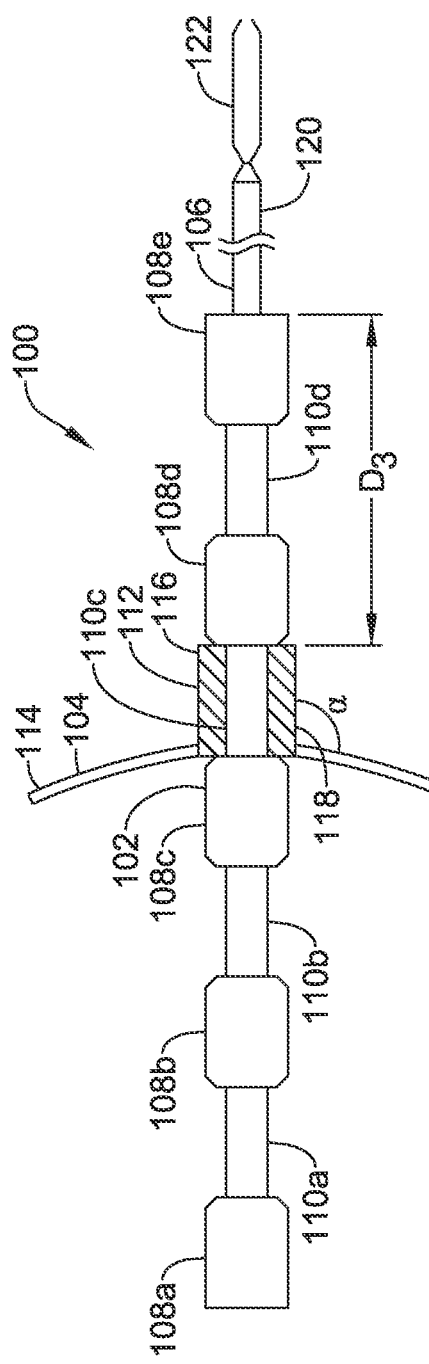

FIGS. 1A-1C illustrate an example of selectively reducing the distance between the proximal anchor 104 and the distal anchor 106, such as moving the proximal anchor 104 along the brace 102 toward the fastener 122. According to various embodiments, the proximal anchor 104 may be placed on the brace 102 (i.e., the ratchet mechanism) by moving elevation 108A through the lumen of the collar 112 of the proximal anchor 104 and advancing the proximal anchor 104 onto the recess 110A to an initial distance ($D_1$) from the distal anchor 106, as shown in FIG. 1A. As discussed above, the collar 112 may be formed of a suitable flexible material so that it may be radially stretched over the elevation 108A and the recess 110A to move the proximal anchor 104 axially along the brace 102. Accordingly, the proximal anchor 104 may fit snuggly around the recess 110A and be coupled to the ratchet mechanism. As such, the elevations 108A and 108B of the ratchet mechanism may be configured to hold the proximal anchor 104 at a first discrete location, thus inhibiting the proximal anchor 104 from moving any further toward or away from the distal anchor 106. Turning to FIG. 8B, in some cases, a physician may move the elevation 108B through the lumen of the collar 112 and advance the proximal anchor 104 onto the recess 110B a distance ($D_2$) from the distal anchor 106, and thus closer to the distal anchor 106 than the first discrete location. As such, the elevations 108B and 108C of the ratchet mechanism may be configured to hold the proximal anchor 104 at a second discrete location, thus inhibiting the proximal anchor 104 from moving any further toward or away from the distal anchor 106. Similarly, turning to FIG. 8C, a physician may then move the elevation 108C through the lumen of the collar 112 and advance the proximal anchor 104 onto the recess 110C a distance ($D_3$)

from the distal anchor 106, and thus closer to the distal anchor 106 than the second discrete position. The elevations 108C and 108D may then hold the proximal anchor 104 at a third discrete location, thus inhibiting the proximal anchor 104 from moving any further toward or away from the distal anchor 106. In some cases, the recesses 110A-110D may have widths larger than the length of the lumen of the collar 112. In this configuration, the proximal anchor 104 may be allowed to move along or oscillate along the recess which it is currently placed a limited amount. As such, the elevations 108A-108E may still be configured to hold the proximal anchor 104 at its current recess location. However, the ability to move along the recess a limited amount may allow the brace 102 to apply a controlled tension or force that can vary slightly to accommodate fluctuations in the tissue of an esophagus and potentially avoid tearing of the tissue. The distance between the proximal anchor 104 and the distal anchor 106 may be periodically reduced over the courses of hours, days, or weeks until the proximal anchor 106 has been moved toward the distal anchor 106 a sufficient amount to connect two disconnected portions of the esophagus.

Figure 2A:
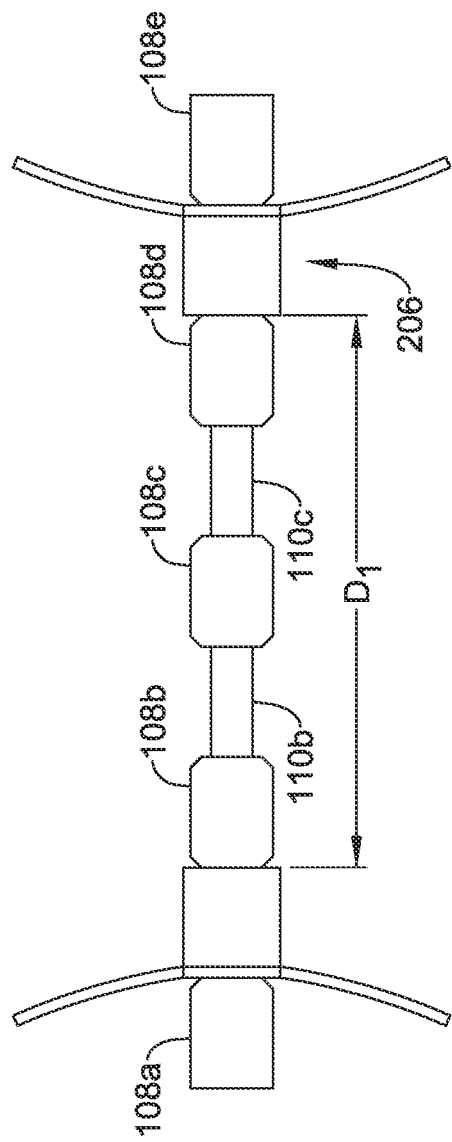
FIGS. 2A-2C illustrate another example of an esophageal atresia bridge device configured for emplacement in the esophagus of a patient.
Figure 2B:
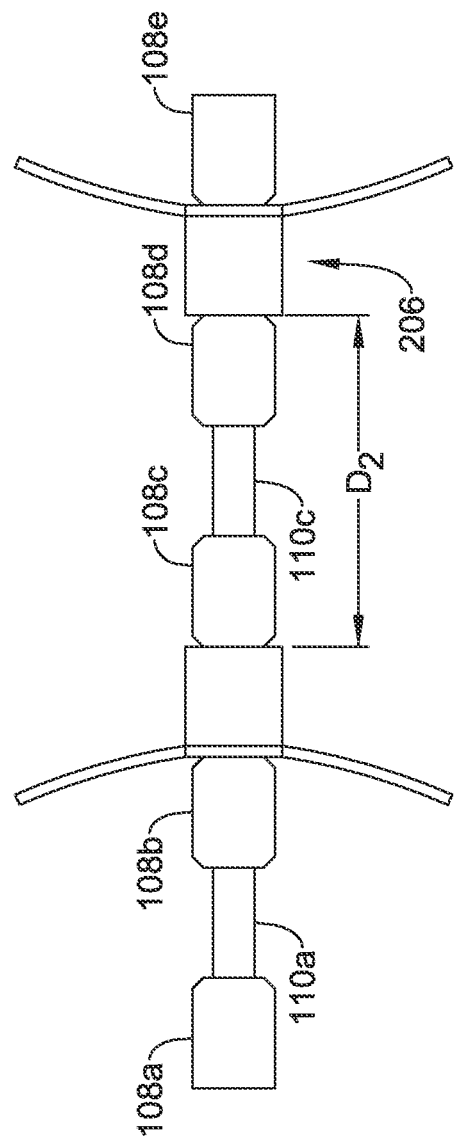
Figure 2C:
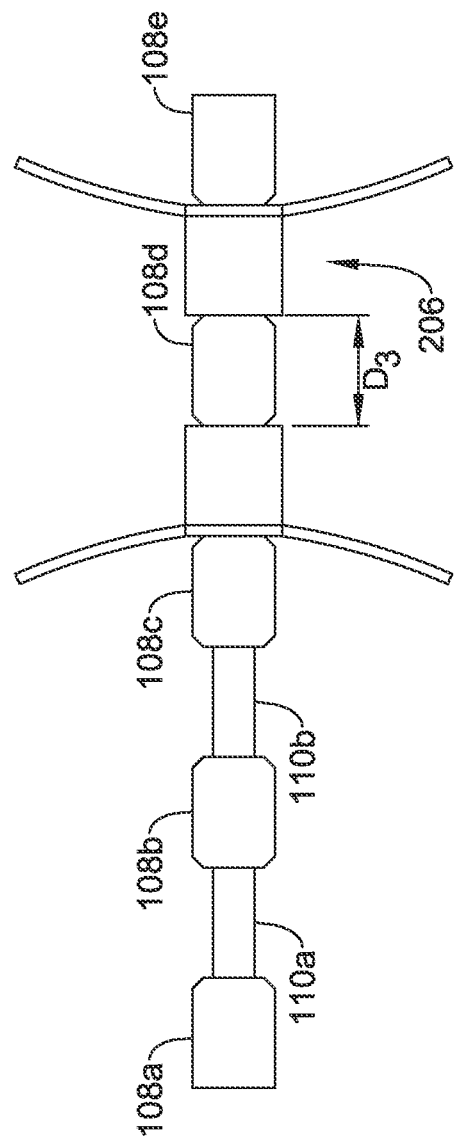

FIGS. 2A-2C illustrate another example of selectively reducing the distance between the proximal anchor 104 and a distal anchor 206, such as moving the proximal anchor 104 along the brace 102 toward the distal anchor 206. In this example, the distal anchor 206 may be configured similar to the proximal anchor 104 and be comprised of similar materials. According to various embodiments, the proximal anchor 104 may be placed on the brace 102 (i.e., the ratchet mechanism) by moving elevation 108A through the lumen of the collar 112 of the proximal anchor 104 and advancing the proximal anchor 104 onto the recess 110A to an initial distance ($D_1$) from the distal anchor 206, as shown in FIG. 2A. As such, the elevations 108A and 108B of the ratchet mechanism may be configured to hold the proximal anchor 104 at a first discrete location, thus inhibiting the proximal anchor 104 from moving any further toward or away from the distal anchor 206. Turning to FIG. 8B, the elevation 108B may be moved through the lumen of the collar 112 and the proximal anchor 104 may be advanced onto the recess 110B a distance ($D_2$) from the distal anchor 106, and thus closer to the distal anchor 206 than the first discrete location. The elevations 108B and 108C may then hold the proximal anchor 104 at a second discrete location, thus inhibiting the proximal anchor 104 from moving any further toward or away from the distal anchor 206. Similarly, turning to FIG. 8C, the elevation 108C may be moved through the lumen of the collar 112 and the proximal anchor 104 may be advanced onto the recess 110C a distance ($D_3$) from the distal anchor 206, and thus closer to the distal anchor 206 than the second discrete position. The elevations 108C and 108D may then hold the proximal anchor 104 at a third discrete location, thus inhibiting the proximal anchor 104 from moving any further toward or away from the distal anchor 206. In some cases, the distal anchor 206 may be advanced along the brace 102 similar to that described for the proximal anchor 104, but in an opposite direction, to move the distal anchor 206 closer to the proximal anchor 104. Moreover, in some examples, the recesses 110A-110D may have widths larger than the length of the lumens of the collars of the proximal and distal anchors. In this configuration, the proximal and/or distal anchor may be allowed to move along or oscillate along the recess which it is currently placed a limited amount. As such, the elevations 108A-108E may still be configured to hold the proximal and/or distal anchors at their current recess location. However, the ability to move along the recess a limited amount may allow the brace 102 to apply a controlled tension or force that can vary slightly to accommodate fluctuations in the tissue of an esophagus and potentially avoid tearing of the tissue. In other instances, the distal anchor 206 may be immovably fixed to the brace 102, such that only the proximal anchor 104 is permitted to be moved longitudinally along the brace 102 to one of a plurality of discrete locations. The distance between the proximal anchor 104 and the distal anchor 206 may be periodically reduced over the courses of hours, days, or weeks until the proximal anchor 106 has been moved toward the distal anchor 206 a sufficient amount to connect two disconnected portions of the esophagus.

Figure 3A:
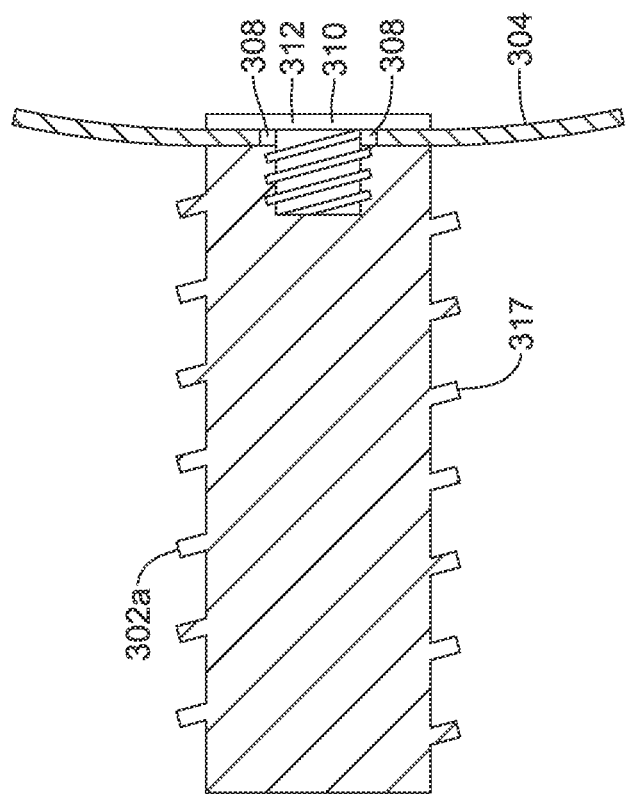
FIG. 3A illustrates a cut away of another example of an esophageal atresia bridge device configured for emplacement in the esophagus of a patient.
Figure 3A:
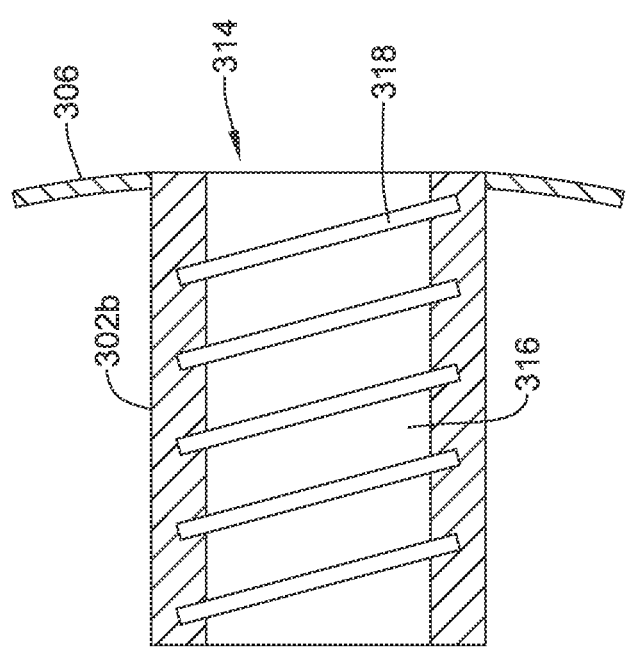

FIG. 3A illustrates a cut away of another example of an esophageal atresia bridge device 300 configured for emplacement in the esophagus of a patient using methods of delivery described herein. As shown, the bridge device 300 may include a brace/link 302A and 302B, a proximal anchor 304, and a distal anchor 306. In some cases, the proximal anchor 304 and the proximal brace portion 302A may be combined, fastened, molded, welded or otherwise joined together. For example, the proximal brace portion 302A may be fixedly secured to the proximal anchor 304, rotationally coupled to the proximal anchor 304, movably attached to the proximal anchor 304, or formed with the proximal anchor 304. In some cases, the distal anchor 306 and the distal brace portion 302B may be combined, fastened, molded, welded or otherwise joined together. For example, the distal brace portion 302B may be fixedly secured to the distal anchor 306, rotationally coupled to the distal anchor 306, movably attached to the distal anchor 306, or formed with the distal anchor 306.

Similar to the bridge device 100, the bridge device 300 may be formed of any biocompatible material suitable for chronic implantation in a patient. In some instances, as shown in FIG. 3A, the brace, including brace portions 302A/302B, may be a screw mechanism that permits infinitely controlled advancement of the proximal anchor 304 towards the distal anchor 306. For instance, the proximal brace portion 302A may include a threaded region threadably engaged with a mating threaded region of the distal brace portion 302B. For instance, the threaded region of the proximal brace portion 302A may be a externally threaded post threadably engaging an internally threaded bore of the distal brace portion 302B, or vice versa.

In some cases, to lessen the probability that the proximal anchor 304 will rotate upon rotational advancement of the proximal brace portion 302A along threaded portion of the distal brace portion 302B, the proximal anchor 304 may have an inner diameter that is configured to fit around a bushing 308 or another separating element. Moreover, a holding screw 310 (or another fastening element) may be placed through an inner diameter of the bushing 308 such that a rim 312 of the holding screw 310 may be adjacent to the proximal anchor 304 or on the opposite side of the brace portion 302A and couple the proximal anchor 304 to the brace portion 302A. Accordingly, as the brace portion 302A rotates during advancement along the threaded portion of the distal brace portion 302B, the proximal anchor 304 may sit on the bushing 308 and avoid being rotated with the brace portion 302A. This may prevent the proximal anchor 304 from rubbing/scrapping against the tissue of an esophagus during advancement of the proximal anchor 304 toward the distal anchor 306 and potentially avoid tearing of the tissue.

In some cases, the screw mechanism may include the brace portion 302A as a post having external threading 317 and the brace portion 302B as a shell having an inner cavity 314 having internal threading 318 configured to mate with the threading of the brace portion 302A. The brace portion 302A may extend through the inner cavity 314 of the brace portion 302B and the distal anchor 306. Moreover, brace portion 302B may allow the brace portion 302A to rotate through the cavity 314.

Figure 3D:
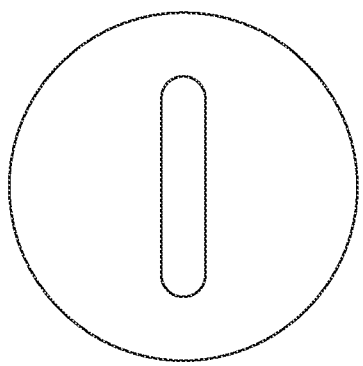
FIGS. 3B-3D depict examples of a holding screw for the esophageal atresia bridge device of FIG. 3A.
Figure 3C:
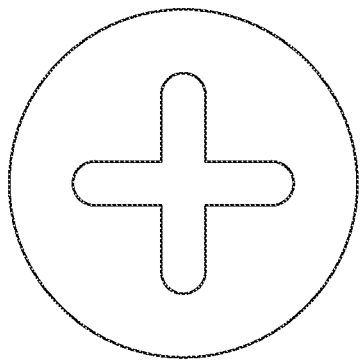
Figure 3B:
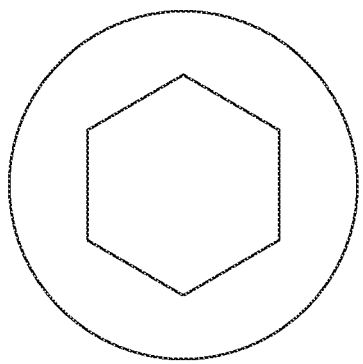

Turning to FIGS. 3B-3D, several examples are shown depicting a driver interface of the proximal brace portion 302A, such as formed in a proximal face of the holding screw 310. FIG. 3B illustrates the driver interface of the brace portion 302A having a hexagon indention configured to receive a hex key to allow a physician to rotate the proximal brace portion 302A using the hex key. FIG. 3C illustrates the driver interface of the brace portion 302A having an "X" indention configured to receive a Phillips head screw driver to allow a physician to rotate the proximal brace portion 302A using the Phillips head screw driver. FIG. 3D illustrates the driver interface of the brace portion 302A having a slit indention configured to receive a flat head screw driver to allow a physician to rotate the proximal brace portion 302A using the flat head screw driver. Although only three embodiments of the driver interface are shown, the driver interface may be configured in any suitable manner that permits a driver to interface with the brace portion 302A to rotate the proximal brace portion 302A relative to the distal brace portion 302B to advance the proximal anchor 304 toward the distal anchor 306.

Figure 3E:
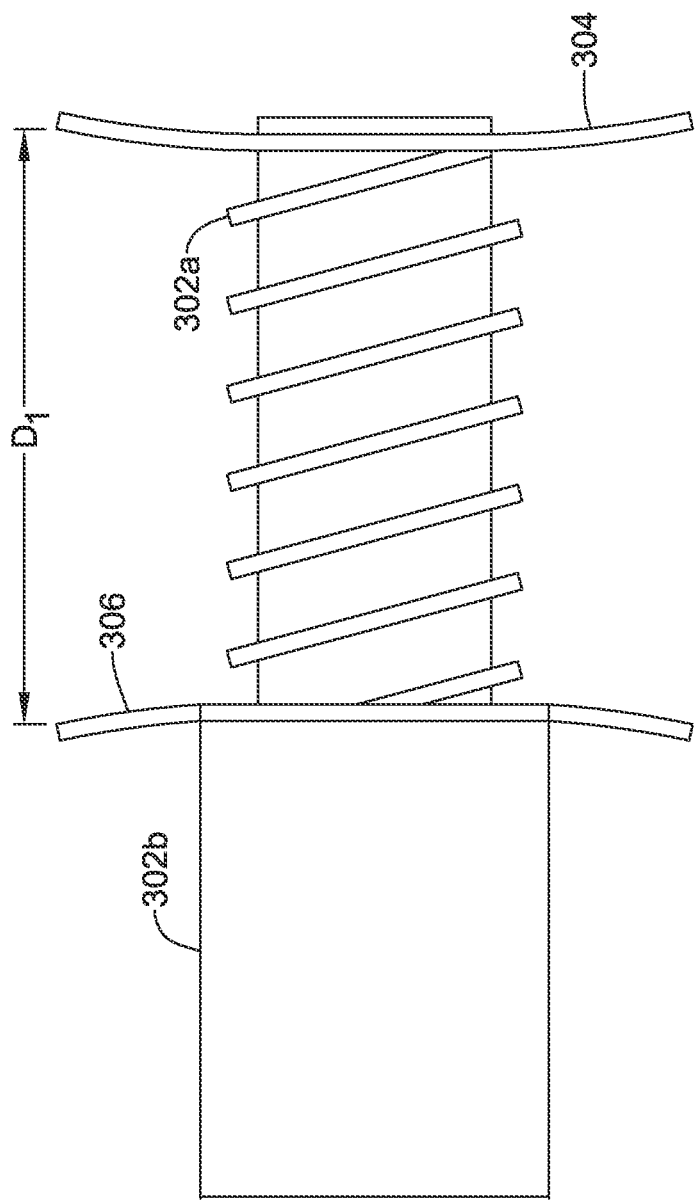
FIGS. 3E-3G illustrate an example of moving the proximal anchor toward the distal anchor of the esophageal atresia bridge device of FIG. 3A.
Figure 3F:
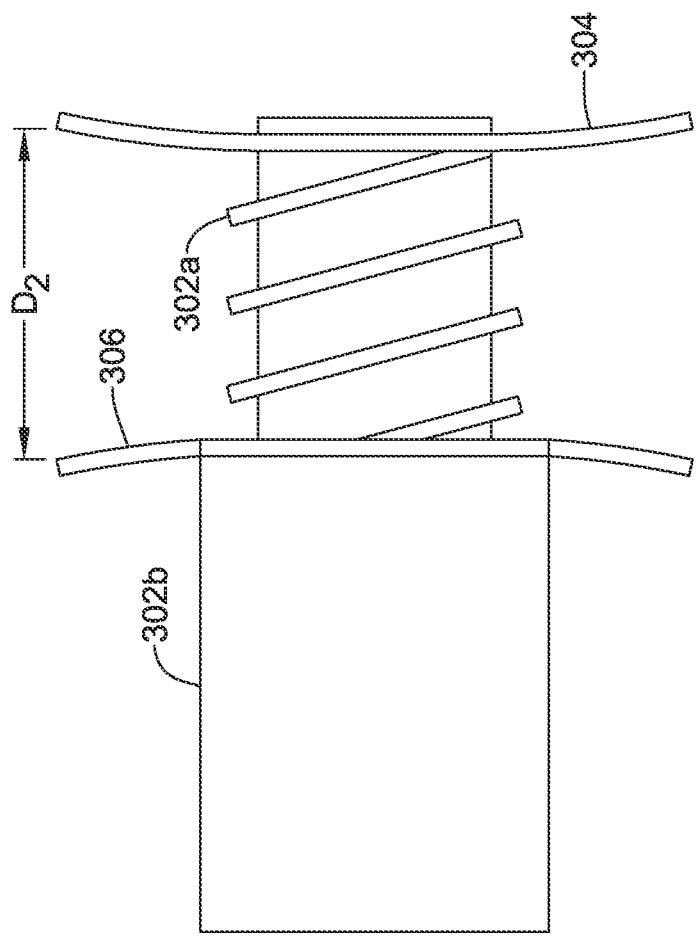
Figure 3G:
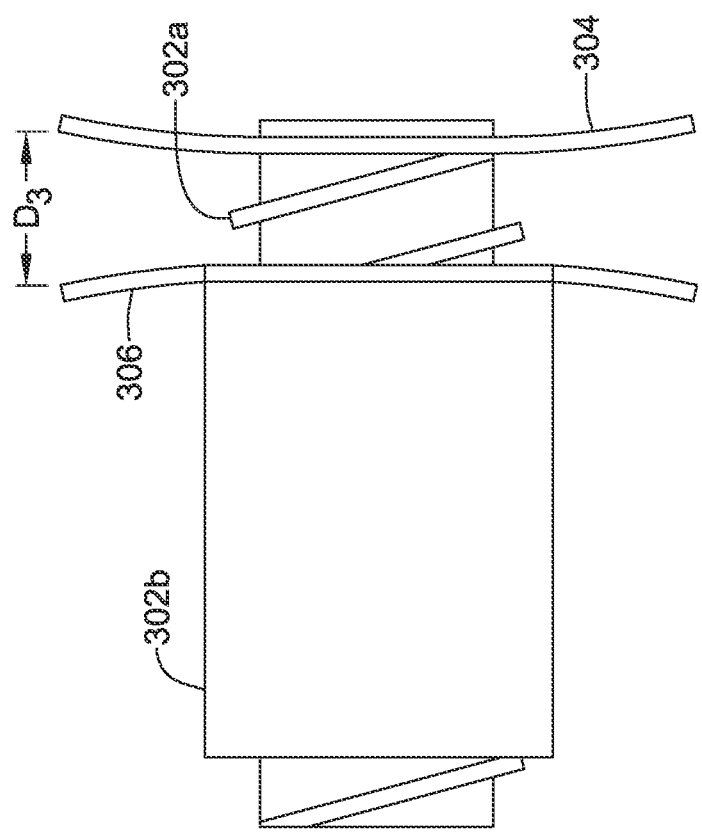

FIGS. 3E-3G illustrate an example of moving the proximal anchor 304 toward the distal anchor 306. According to various embodiments, the threaded portion 317 of the proximal brace portion 302A may be threadably engaged with the threaded portion 318 of the distal brace portion 302B, as shown in FIG. 3E, such that the proximal anchor 304 is an initial distance ($D_1$) from the distal anchor 306. Turning to FIG. 3F, in some cases, a physician may use a tool to rotate the proximal brace portion 302A relative to the distal brace portion 302B to advance the proximal anchor 304 toward the distal anchor 306 to a desired distance ($D_2$) from the distal anchor 306. As such, the threads of the proximal brace portion 302A and the threads of the distal brace portion 302B may be configured to hold the proximal anchor 304 from moving any further toward or away from the distal anchor 306 once the desired distance is reached. Similarly, turning to FIG. 3G, a physician may use a tool to further rotate the proximal brace portion 302A relative to the distal brace portion 302B to further advance the proximal anchor 304 toward the distal anchor 306 to a desired distance ($D_3$) from the distal anchor 306. The threads of the proximal brace portion 302A and the threads of the distal brace portion 302B may then hold the proximal anchor 304 from moving any further toward or away from the distal anchor 306 once the desired distance is reached. Further adjustment of the distance between the proximal anchor 304 and the distal anchor 306 may be periodically performed over the course of hours, days, or weeks until the proximal anchor 304 has been moved toward the distal anchor 306 a sufficient amount to connect two disconnected portions of the esophagus.

Figure 4A:
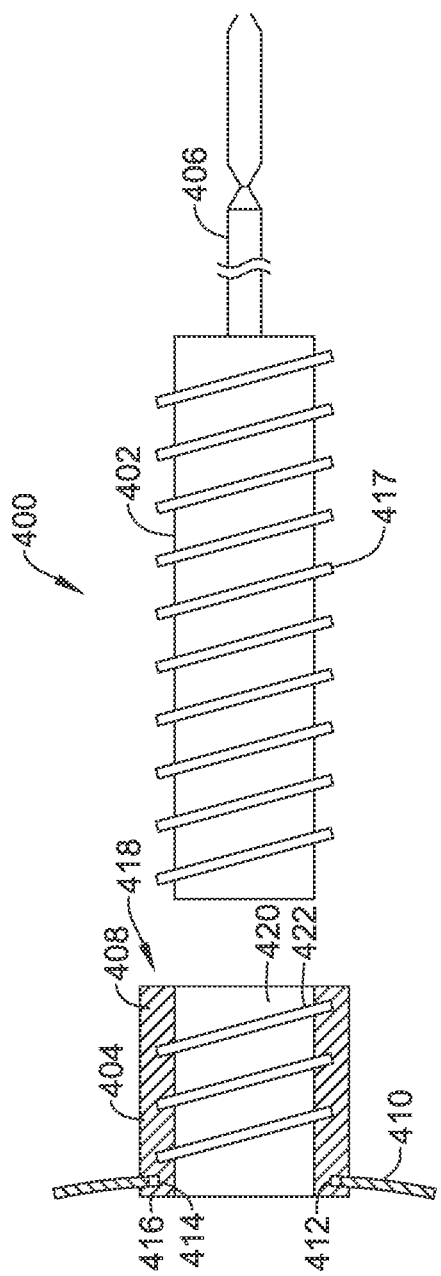
FIG. 4A illustrates a cut away of another example of an esophageal atresia bridge device configured for emplacement in the esophagus of a patient.

FIG. 4A illustrates a cut away of another example of an esophageal atresia bridge device 400 configured for emplacement in the esophagus of a patient using methods of delivery described herein. As shown, the bridge device 400 may include an elongate member or a brace/link 402, a proximal anchor 404, and a distal anchor 406. In some cases, the distal anchor 406 and the brace 402 may be combined, fastened, molded, welded or otherwise joined together. For example, the brace 402 may be fixedly secured to the distal anchor 406, rotationally coupled to the distal anchor 406, movably attached to the distal anchor 406, or formed with the distal anchor 406.

Similar to the bridge device 100, the bridge device 400 may be formed of any biocompatible material suitable for chronic implantation in a patient. In some instances, as shown in FIG. 4A, the brace 402 may be a screw mechanism that permits infinitely controlled advancement of the proximal anchor 404 towards the distal anchor 406. For instance, the proximal anchor 404 may include a threaded region threadably engaged with a mating threaded region of the brace 402. For instance, proximal anchor 404 may include an internally threaded collar mating with an externally threaded region of the brace 402, such as a threaded post, or vice versa.

According to various embodiments, the proximal anchor 404 may comprise a rotatable member or collar 408 defining a lumen and an enlarged portion or a securing mechanism(s) 410 for engaging the proximal section of the patient's esophagus. In some cases, the securing mechanism(s) 410 may include a radially extending flange. In some cases, to lessen the probability that the securing mechanism(s) 410 will rotate upon advancement of the proximal anchor 404, the securing mechanism(s) 410 may have an inner diameter that is configured to fit around a bushing 412 or another separating element and a recess 414 of the collar 408. Moreover, the collar 408 may also have a ridge 416 that is adjacent to the securing mechanism(s) 410 and holds the securing mechanism(s) 410 in place when the securing mechanism(s) 410 is in the recess 414. Accordingly, as the collar 408 rotates during advancement of the proximal anchor 404 toward the distal anchor 406, the securing mechanism(s) 410 may not be rotated. This may prevent the securing mechanism(s) 410 from rubbing/scrapping against the tissue of an esophagus during advancement and potentially avoid tearing of the tissue. In some cases, the brace 402 may be a screw having external threading 417 and the collar 408 may be a shell having internal threading 418 that extends through the lumen of the collar 408. Moreover, an inner wall 420 of the collar 408 may be comprised of threads 418 (e.g., "female threads") to allow the collar 408 to rotate over the screw brace 402.

Figure 4C:
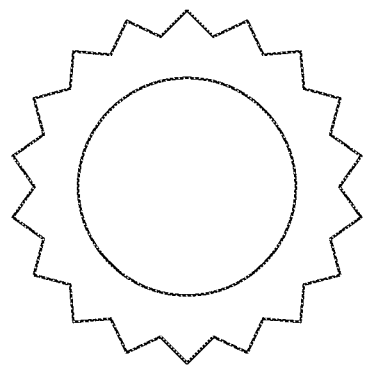
FIGS. 4B-4C depict examples of a driver engagement feature of the esophageal atresia bridge device of FIG. 4A.
Figure 4B:
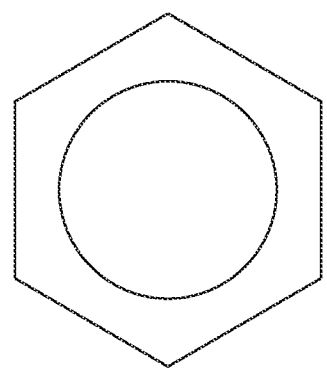

Turning to FIGS. 4B and 4C, examples are shown depicting a driver interface of the collar 408. FIG. 4B illustrates the driver interface of the collar 408 having a hexagon shape to receive a tool, such as a wrench or socket, to allow a physician to rotate the collar 408 using the tool. FIG. 4C illustrates the driver interface of the collar 408 having a circular shape with jagged edges configured to receive a similar circular jagged edge shaped tool, such as a wrench or socket, to allow a physician to rotate the collar 408 using the circular jagged edge shaped tool. Although only two shapes of the driver interface are shown, the driver interface of the collar 408 may be configured in any suitable manner that allows a physician to rotate the collar 408 relative to the brace 402 to advance the proximal anchor 404 toward the distal anchor 406.

Figure 4D:
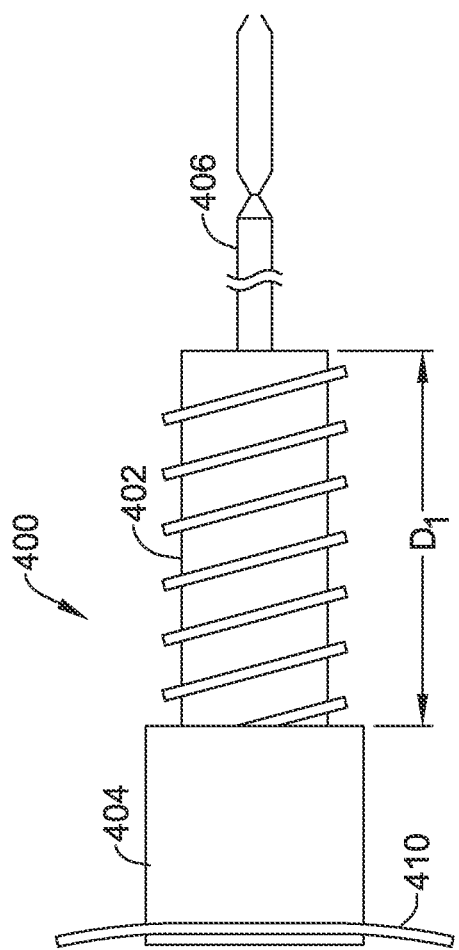
FIGS. 4D-4F illustrate an example of moving the proximal anchor toward the distal anchor of the esophageal atresia bridge device of FIG. 4A.
Figure 4E:
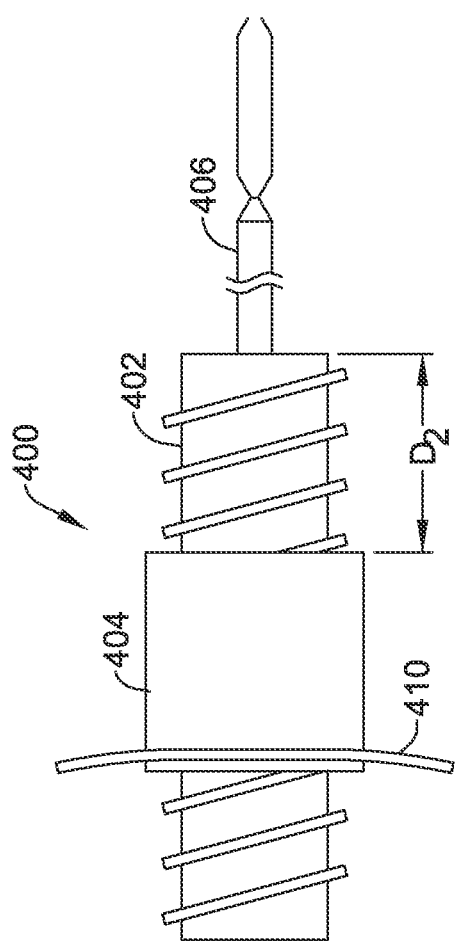
Figure 4F:
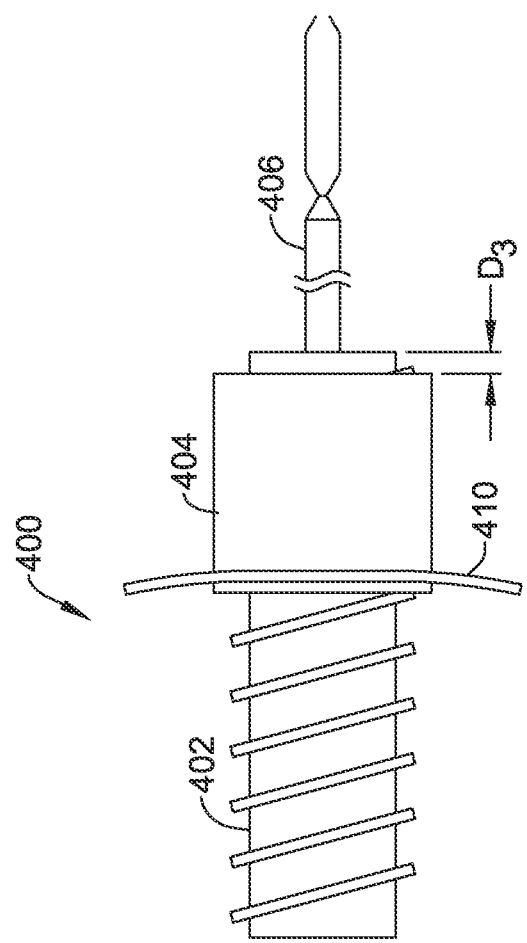

FIGS. 4D-4F illustrate an example of moving the proximal anchor 404 toward the distal anchor 406. According to various embodiments, an end of the screw brace 402 may be placed in the threaded bore of the collar 408 of the proximal anchor 404 and aligned with the threads such that the proximal anchor 404 is an initial distance ($D_1$) from the distal anchor 406, as shown in FIG. 4D. Turning to FIG. 4E, in some cases, a physician may use a tool to rotate the collar 408 relative to the brace 402 to advance the proximal anchor 404 toward the distal anchor 406 to a desired distance ($D_2$)

from the distal anchor 406. As such, the threads of the screw brace 402 and the threads of the collar 408 may be configured to hold the proximal anchor 404 from moving any further toward or away from the distal anchor 406 once the desired distance is reached. Similarly, turning to FIG. 4F, a physician may use a tool to further rotate the collar 408 relative to the brace 402 to further advance the proximal anchor 404 toward the distal anchor 406 to a desired distance ($D_3$) from the distal anchor 406. The threads of the screw brace 402 and the threads of the collar 408 may then hold the proximal anchor 404 from moving any further toward or away from the distal anchor 406 once the desired distance is reached. Further adjustment of the distance between the proximal anchor 404 and the distal anchor 406 may be periodically performed over the course of hours, days, or weeks until the proximal anchor 404 has been moved toward the distal anchor 406 a sufficient amount to connect two disconnected portions of the esophagus (e.g., to surgically attach the proximal section or the proximal pouch of the patient's esophagus to the distal section or the distal pouch of the patient's esophagus).

FIGS. 5A-5F show access to and implantation of the esophageal atresia bridge device 100 from FIGS. 1A-1C. Starting with FIGS. 5A and 5B, the bridge device 100 may be connected to a delivery device 500 that may include a detachable handle assembly 502 and a hollow tube 504. In some cases, the handle assembly 502 may include a trigger 506 that, when pulled, actuates the fastener 122 of the distal anchor 106. In some instances, when the trigger 506 is pulled, the fastener 122 may close and when the trigger 506 is turned, the fastener 122 may be locked into the closed position. Access to an esophagus (see FIGS. 5C-5F) may be obtained through the mouth of the patient or using standard access techniques known in the art. In another technique, the stomach may be punctured with a hollow needle or trocar, for example under ultrasound guidance, to gain access to the patient's stomach. Moreover, other implanting techniques may be used instead.

Figure 5A:
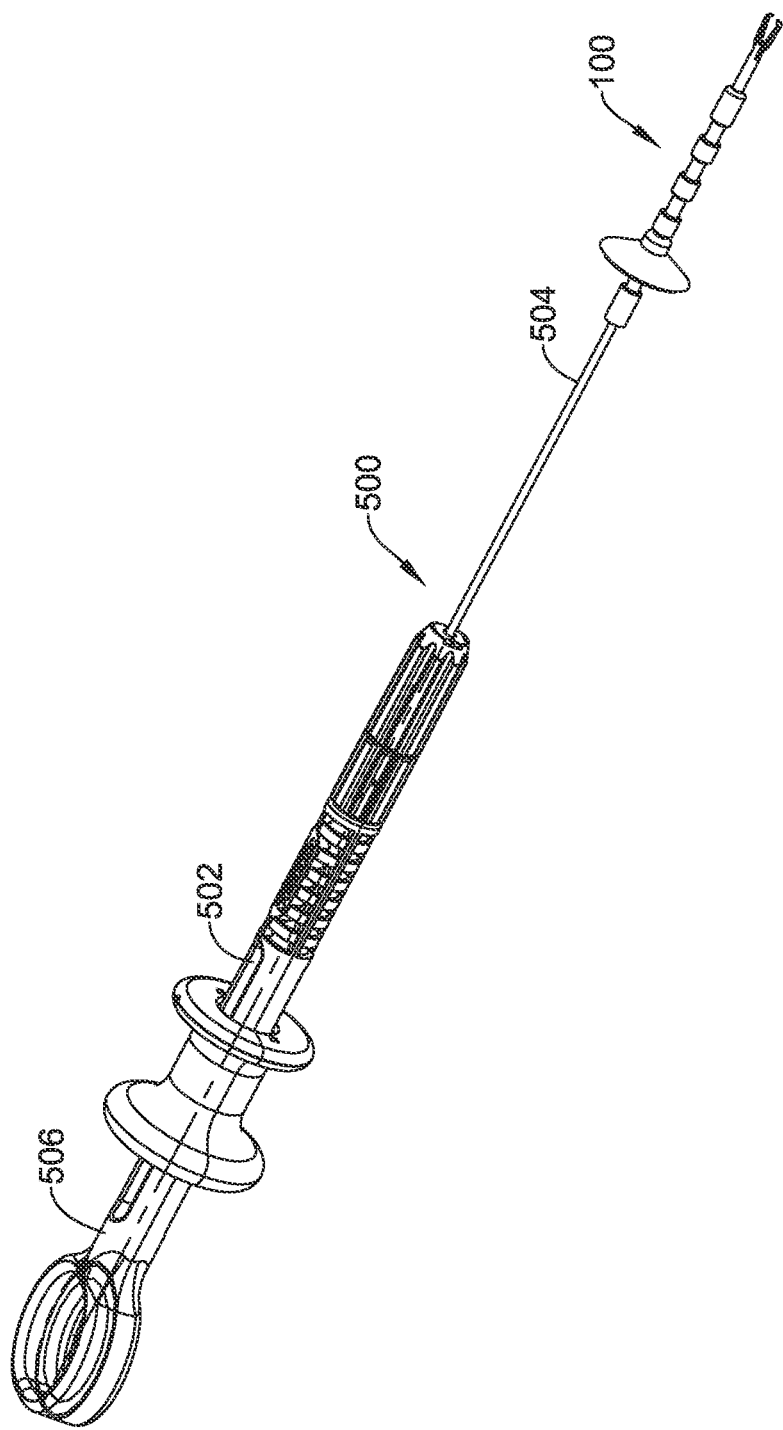
FIGS. 5A-5F show access to and implantation of the esophageal atresia bridge device of FIGS. 1A-1C.
Figure 5B:
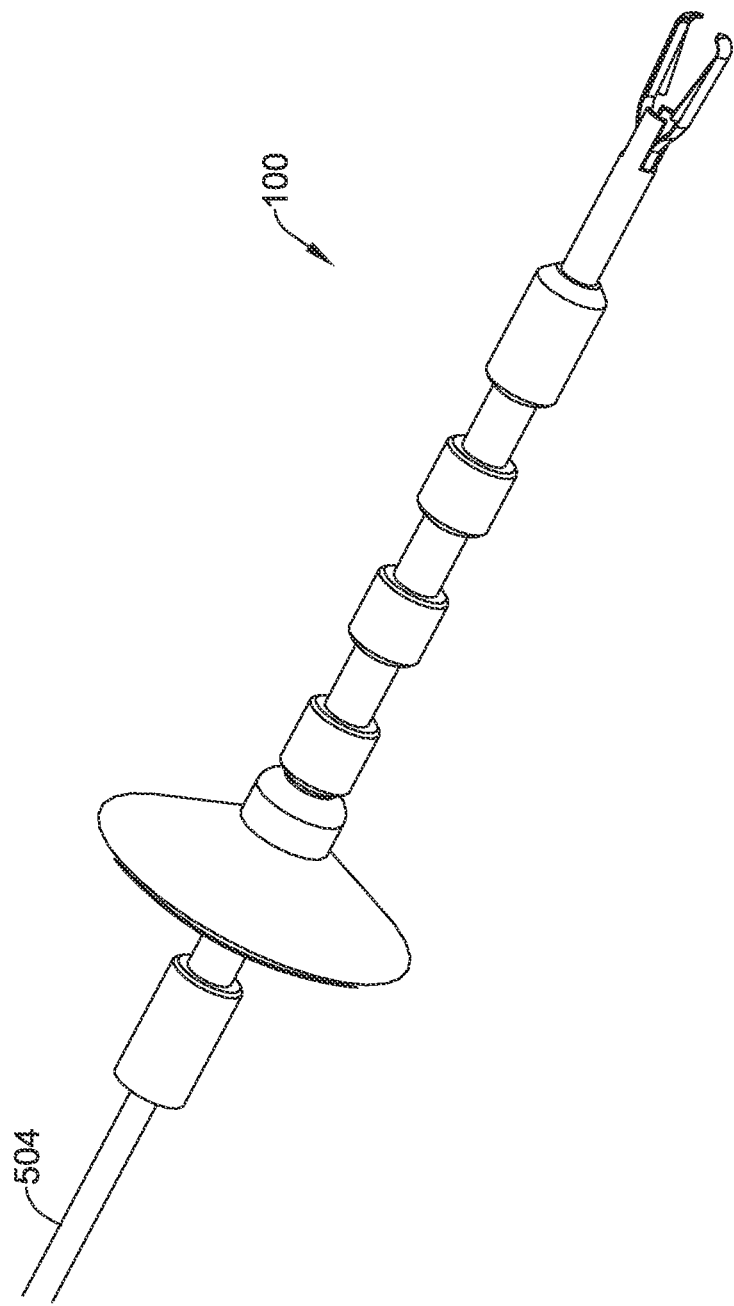
Figure 5C:
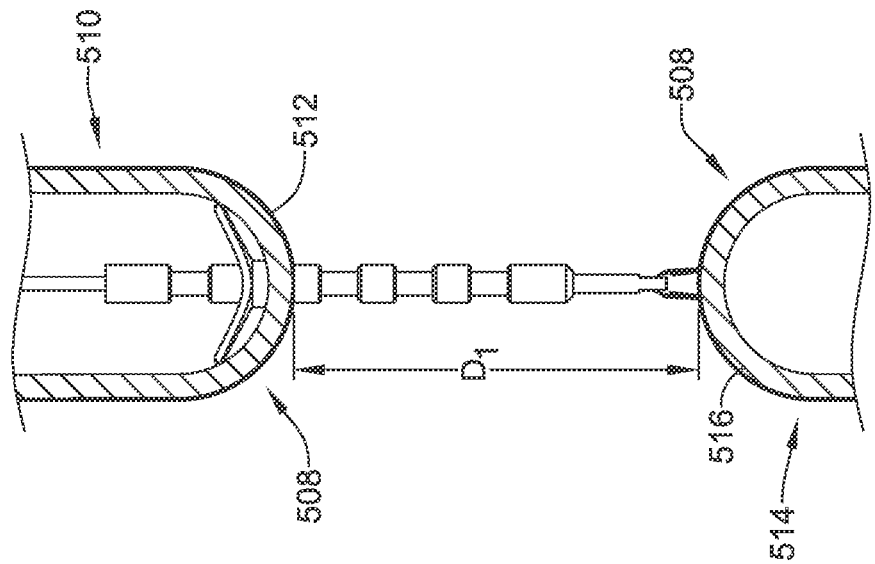

Turning to FIG. 5C, into the access (e.g., the mouth), an introducer sheath may be inserted and advanced to a location near an end 512 of a proximal section 510 of the esophagus 508. Contrast injection may be useful to visualize the proximal section 510 of the esophagus 508. The delivery device 500 with the bridge device 100 may then be introduced through the introducer sheath. In an example, the delivery device 500 with the bridge device 100 may be advanced to a desired location relative to the end 512 of the proximal section 510. The fastener 122 of the bridge device 100, which may be deflectable or steerable, can then extend from the proximal section 510 to an end 516 of a distal section 514 of the esophagus 508, spaced apart and detached from the proximal section 510. In some cases, the fastener 122 may be configured to penetrate through the end 512 of the proximal section 510 and advanced to the end 516 of the distal section 514 of the esophagus 508. In some examples, the trigger 506 of the delivery device 500 may then be actuated to close the fastener 122 and turned to lock the fastener 122 in the closed position. As such the distal anchor 106 may now be anchored to the distal section 514 of the esophagus. Furthermore, the proximal anchor 104 may be expanded or deployed in the proximal section 510 of the esophagus 508 into engagement with tissue of a luminal wall of the proximal section 510 of the esophagus 508.

Figure 5D:
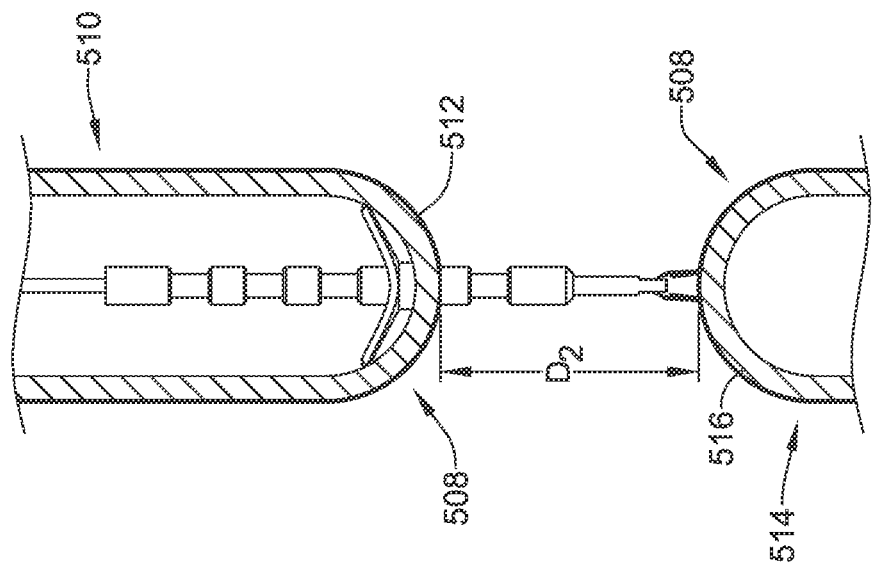
Figure 5E:
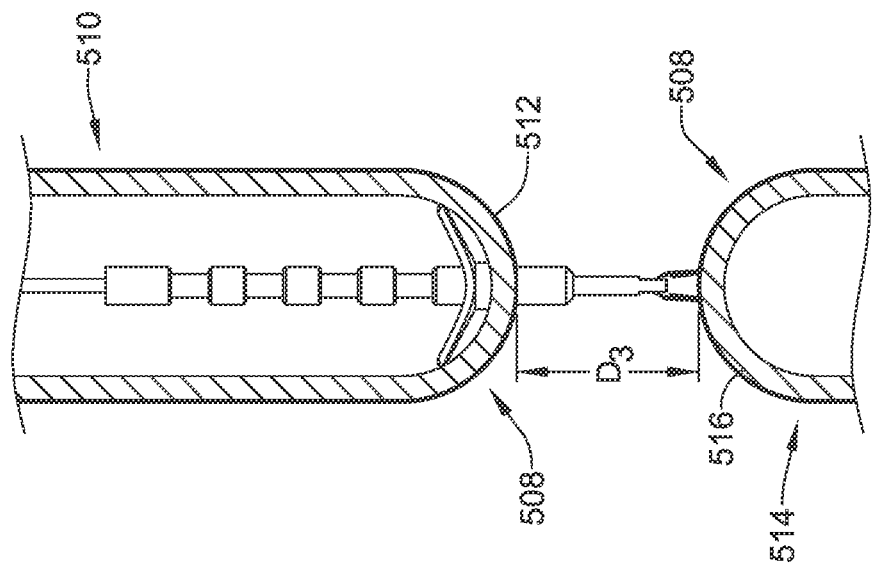

According to various embodiments, the proximal anchor 104 may then be advanced along the brace 102 to an initial distance ($D_1$) from the distal anchor 106. In some cases, the securing mechanism(s) 114 of the proximal anchor 104 may be configured to push against and engage the tissue of the luminal surface of the proximal section 510 of the esophagus 508 near the end 512 of the proximal section 510 and anchor the proximal anchor 104 to the proximal section 510 of the esophagus 508. In some instances, in this position, the bridge device 100 may apply a controlled tension that pulls the proximal section 510 of the esophagus 508 towards the distal section 514 of the esophagus 508 and stretch the esophagus over time. Turning to FIG. 5D, after the esophagus has had time to stretch, the proximal anchor 104 may be advanced toward the distal anchor 106 to a distance ($D_2$) from the distal anchor 106. Accordingly, the bridge device 100 may again apply a controlled tension that pulls and stretches the proximal section 510 of the esophagus 508 further towards the distal section 514 of the esophagus 508. Similarly, turning to FIG. 8D, after the esophagus has had time to stretch, the proximal anchor 104 may be further advanced toward the distal anchor 106 to a distance ($D_3$) from the distal anchor 106. As such, the bridge device 100 may again apply a controlled tension that further pulls and stretches the proximal section 510 of the esophagus 508 further towards the distal section 514 of the esophagus 508. In some cases, the proximal anchor 104 may be allowed to move slightly or oscillate along the recess it is currently placed. As such, the bridge device 100 may apply a controlled tension or force that can vary slightly to accommodate fluctuations in the tissue of the esophagus 508 and potentially avoid tearing of the tissue.

Figure 5F:
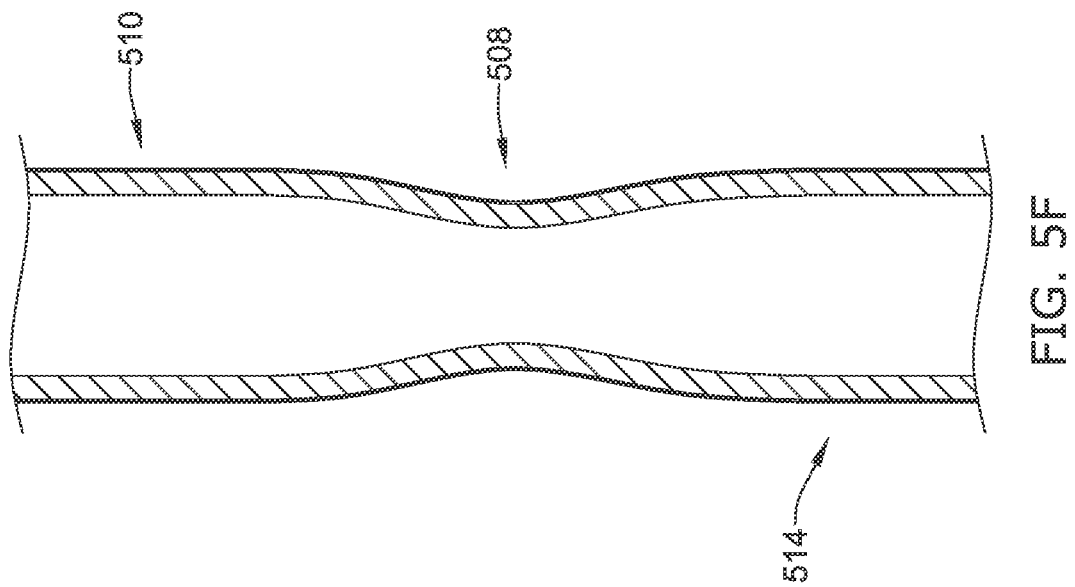

Turning to FIG. 5F, when the proximal section 510 is close enough to the distal section 514 of the esophagus 508 the bridge device 100 may be removed and the disconnected portions of the esophagus may be connected. Accordingly, the proximal section 510 may be connected to the distal section 514, such as with sutures (i.e., the proximal section 510 and/or the distal section 514 have been stretched enough such that any tension administered to connect the proximal section to the distal section will not cause unwanted tearing of the tissue of the proximal section or the distal section).

It is noted that the medical procedure described above can be performed with any of the devices described herein. For instance, the distal anchor 206, 306 or 406 may be advanced into the distal section 514 of the esophagus and expanded to anchor the device to the distal section 514 of the esophagus, while the proximal anchor 104, 304 or 404 is expanded or deployed in the proximal section 510 of the esophagus. Thereafter, the proximal anchor may be controllably moved toward the distal anchor until the proximal section 510 of the esophagus is sufficiently drawn to the distal section 514 of the esophagus to connect the proximal and distal sections 510/514 of the esophagus together.

Figure 6:
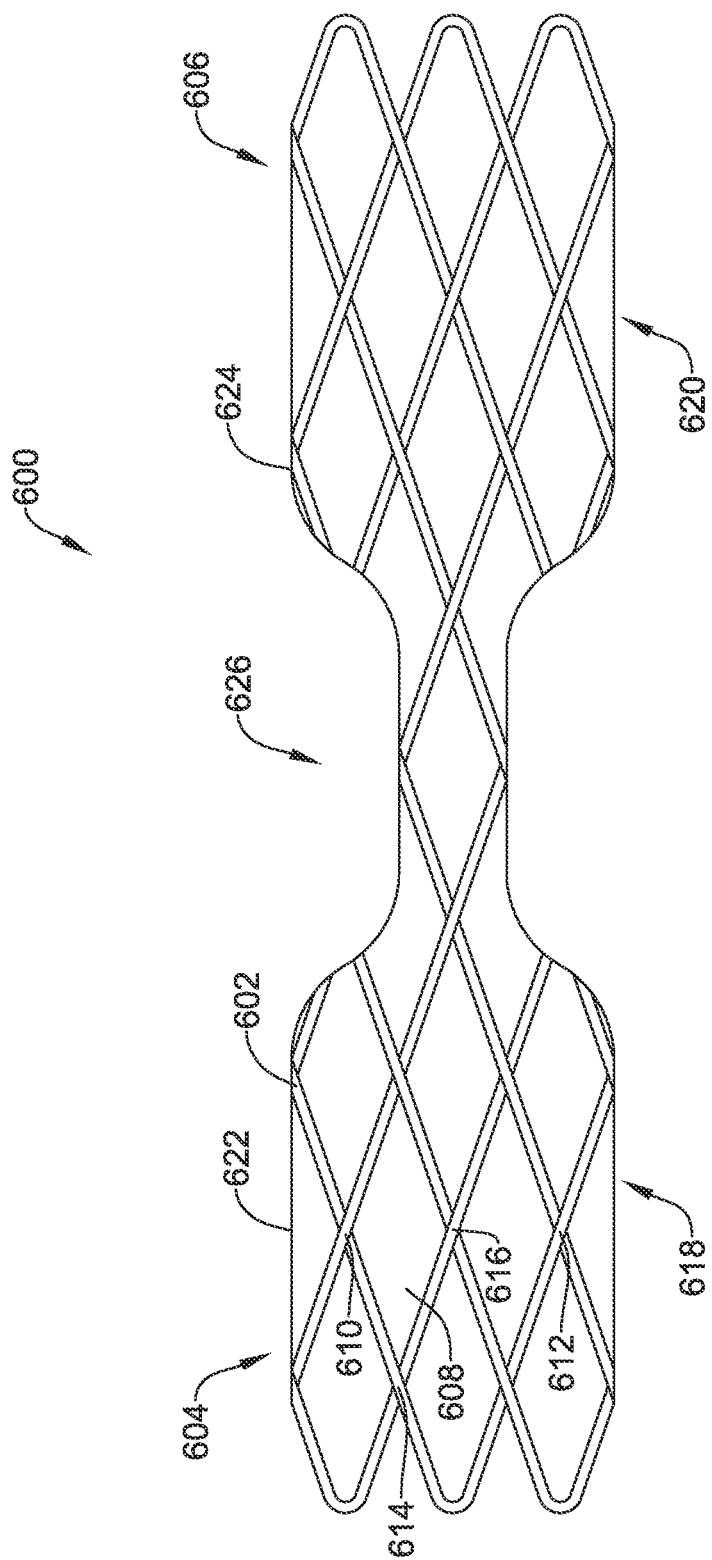
FIG. 6 illustrates another example of an esophageal atresia bridge device configured for emplacement in the esophagus of a patient.

FIG. 6 illustrates another example of an esophageal atresia bridge device 600 configured for emplacement in the esophagus of a patient using methods of delivery described herein. In some cases, the bridge device 600 may be a radially expandable stent formed from a plurality of braided wires 602. In certain embodiments, the braided wires 602 may have a first set of wire segments that extend parallel to one another in a first helical direction and a second set of wire segments that extend parallel to one another in a second helical direction, opposite of the first helical direction. As such, the first set of wire segments and the second set of wire segments may cross or intersect multiple times at the cross-over points to form a braid pattern. In some cases, the braid pattern may be uneven or non-uniform because the spacing between the individual wire segments from either set of wire segments may vary or the angle at which the wire segments cross may vary. In some instances the braid pattern may be in a one-under and one-over braiding configuration in which a single wire segment extending in the first helical direction intersects a single wire segment extending in the second helical direction at each crossover point. In the one-under and one-over braiding configuration, a wire segment from the first set of wire segment may be located above (radially outward of) a first wire segment from the second set of wire segments at a first crossing (i.e., crossover point), then below a second wire segment from the second set of wire segments at a second crossing (i.e., crossover point), then above a third wire segment from the second set of wire segments at a third crossing (i.e., crossover point), and continue in this alternating pattern from a proximal end 604 of the bridge device 600 to a distal end 606 of the bridge device 600. Moreover, the other wires from the braided wires 602 may also be braided in this alternating pattern from the proximal end 604 to the distal end 606. In various embodiments, the one-under and one-over configuration of the wires may define a plurality open cells (e.g., open cell 608). Open cells may be openings through the tubular wall of the bridge device 600. The open cells may have a parallelogram shape, having upper apexes, lower apexes, and side apexes formed by the crossover points (e.g., crossover points 610-616). The braided wires 602 are not limited to the one-under and one-over configuration. In some alternate configurations, the braided wires 602 may be braided in a two-under and a two-over pattern. Other braiding patterns known in the art may also be suitably used. Further, in some cases, the braided wires 602 may be paired with one another and braided by using each pair of wires in a one-under and one-over pattern. The pairs of wires may be the same or may be different (e.g., may have the same or different dimensions, shapes and/or materials of construction). Moreover, the pairs of wires may suitably be braided in other braided patterns, such as but not limited to, for example, the two-under and two-over pattern.

According to various embodiments, the braided wires 602 may be made from any suitable implantable material, including without limitation nickel-titanium alloy (e.g., nitinol), stainless steel, cobalt-based alloy such as Elgiloy®, platinum, gold, titanium, tantalum, niobium, polymeric materials and combinations thereof. Useful polymeric materials may include, for example, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, natural silk, polyvinyl chloride, polytetrafluoroethylene, including expanded polytetrafluoroethylene (ePTFE), fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, and copolymers and combinations thereof. Further, useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly (phosphate ester) and the like. Wires made from polymeric materials may also include radiopaque materials, such as metallic-based powders, particulates or pastes which may be incorporated into the polymeric material. For example, the radiopaque material may be blended with the polymer composition from which the polymeric wire is formed, and subsequently fashioned into the stent as described herein. Alternatively, the radiopaque material may be applied to the surface of the metal or polymer stent. In either embodiment, various radiopaque materials and their derivatives may be used including, without limitation, bismuth, barium and its derivatives such as barium sulphate, tantalaum, tungsten, gold, platinum and titanium, to name a few. Additional useful radiopaque materials may be found in U.S. Pat. No. 6,626,936, which is herein incorporated in its entirety by reference. Metallic complexes useful as radiopaque materials are also contemplated. The bride device 600 may be selectively made radiopaque at desired areas along the wire or may be fully radiopaque, depending on the desired end-product and application. Further, the braided wires 602 may have an inner core of tantalum, gold, platinum, iridium or combinations thereof and an outer member or layer of nitinol to provide a composite wire for improved radiopacity or visibility. In some cases, the inner core may be platinum and the outer layer may be nitinol. In some cases, the inner core of platinum may represent about at least 10% of the wire based on the overall cross-sectional percentage. Moreover, nitinol that has not been treated for shape memory such as by heating, shaping and cooling the nitinol at its martensitic and austenitic phases, may also useful as the outer layer. Further details of such composite wires may be found in U.S. Pat. No. 7,101,392, the contents of which is incorporated herein by reference.

In some cases, the bridge device 600 may include a proximal portion 618, an intermediate portion 626, and a distal portion 620. In some examples, the proximal portion 618 may include a proximal anchor 622 and the distal portion 620 may include a distal anchor 624. In some cases, the proximal anchor 622 and the distal anchor 624 may be a flare, flange, or an elevation of the braided wires 602. That is, the proximal anchor 622 may be flared end region of the stent having a larger radius compared to the intermediate portion 626, and the distal anchor 624 may be a flared end region of the stent having a larger radius compared to the intermediate portion 626. In some cases, the proximal anchor 622 and the distal anchor 624 may be configured to radially expand to push against and engage tissue of the patient when the bridge device 600 is implanted inside the proximal section and the distal section of the esophagus of the patient. In some cases, the anchors 622 and 624 may include hooks, pins, tines, and/or any other suitable element that can assist in anchoring the bridge device 600 to the esophagus of the patient. In some examples, the anchors 622 and 624 may be shaped such that the anchors 622 and 624 may potentially have an optimal anchoring configuration. For instance, in some cases, the anchors 622 and 624 may be geometrically shaped and have an angle of incline from the proximal and distal portions 618 and 620 that allow the anchors 622 and 624 to have an optimal amount of surface area to engage the tissue of the esophagus. For example, in some cases, the anchors 622 and 624 may have a 90° incline, approximately, from the proximal and distal portions 618 and 620 and relatively flat edges to engage the tissue of the esophagus. In some cases, the anchors 622 and 624 may have an angle of incline of approximately 100°, 115°, 130°, 160°, etc. and have rounded edges, pointed edges, etc. In some cases, the anchors 622 and 624 may be configured to move, retract, or compress towards the bridge device 600 to prevent tearing of the tissue when implanted in the esophagus.

Figure 7A:
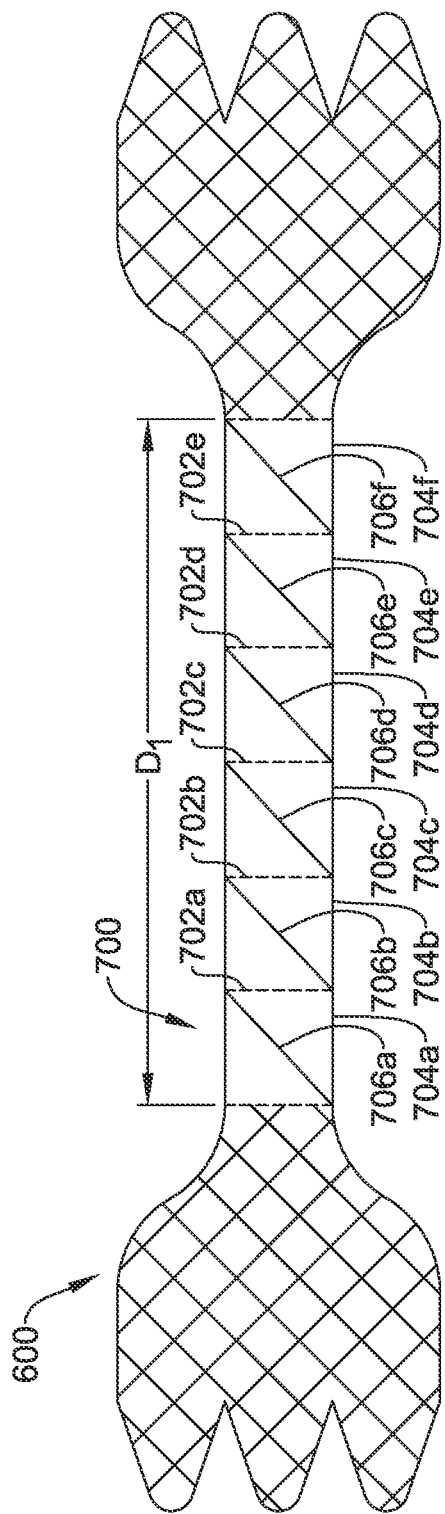
FIGS. 7A-7C illustrate an example of expansion of the intermediate portion of the esophageal atresia bridge device of FIG. 6 as a brace/link is removed.
Figure 7B:
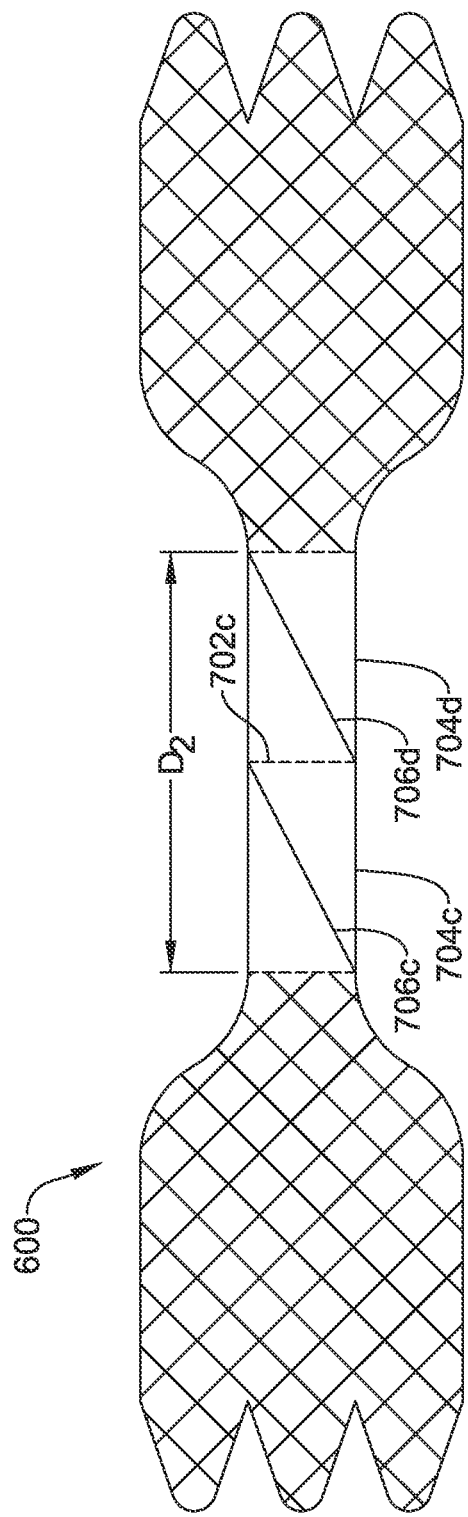
Figure 7C:
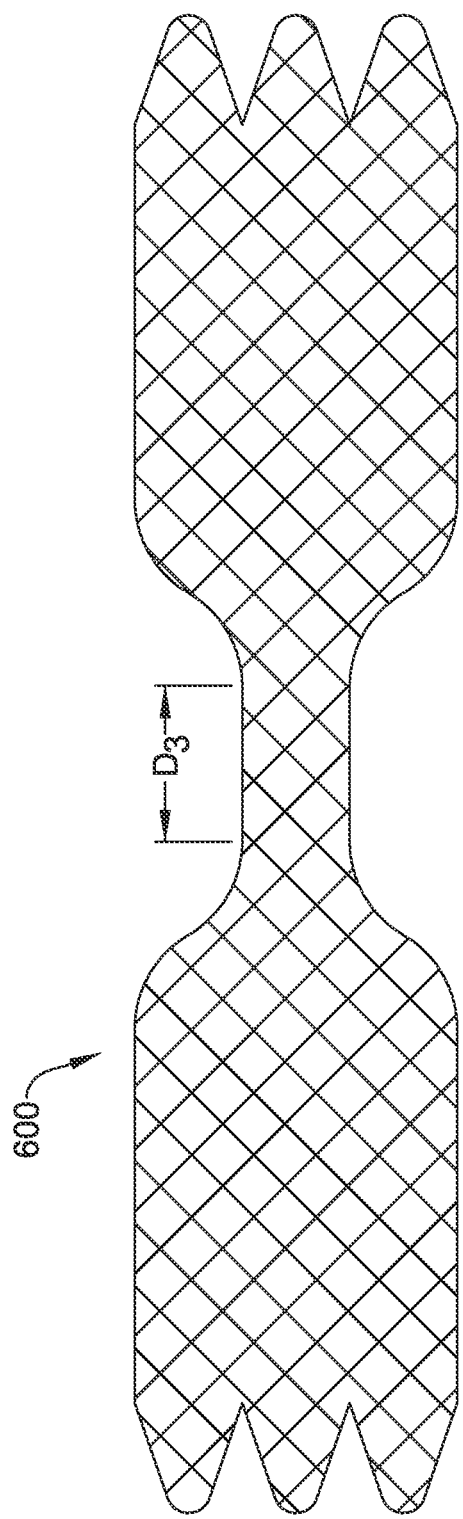

FIGS. 7A-7C illustrate an example of expansion of the intermediate portion 626 as a brace/link (e.g., a sheath 700) is removed from the bridge device 600. The sheath 700 may be comprised of materials known in the art for sheaths. In some cases, the sheath 700 may have a generally consistent surface and cross-section. In some embodiments, the sheath 700 may include one or more, or a plurality of frangible regions, configured to separate from the remainder of the sheath 700. For instance, the sheath 700 may have areas that are weaker than other portions to provide preferential tear lines 702A-702E (e.g., score lines, perforations, and/or thinner portions), so that the sheath 700 may tear at the preferential tear lines 702A-702E. In some instances, the preferential tear lines 702A-702E may be molded, cut, etched, or otherwise formed in the sheath 700. In other instances, the preferential tear lines 702A-702E can be created by softening the desired area of the sheath 700 with heat, or otherwise deforming the structure of the sheath material at the desired location. In some cases, the preferential tear lines 702A-702E may be selectively positioned about the sheath 700 so that portions of the sheath 700 are removed or detached in a selected and controlled manner. For instance, the preferential tear lines 702A-702E may be positioned such that the sheath 700 includes removable sections 704A-704F, which may be separable from one another. Optionally, the removable sections 704A-704F may be initially joined and the sheath 700 may include string(s) 706A-706F, cords, ropes, strands, or any other element configured to separate a removable section from the remainder of the sheath 700 at the preferential tear line 702A-702E.

As shown in FIG. 7A, in some cases, the sheath 700 may be placed onto the intermediate portion 626 of the bridge device 600 using methods known in the art. In some cases, the intermediate portion 626 may be restrained in a radially compressed configuration by the sheath 700. According to various embodiments, the sheath 700 may radially compress the intermediate portion 626 to axially elongate the intermediate portion 626 such that the proximal portion 618 is an initial distance ($D_1$) from the distal portion 620. Turning to FIG. 7B, in some instances, a physician may pull on the strings (e.g., strings 706A-706B and 706E-706F) or otherwise manipulate the sheath 700 of the bridge device 600 to detach the removable sections (e.g., removable section 704A-704B and 704E-704F) at the preferential tear lines (e.g., preferential tear lines 702A-702B and 702D-702E) and tear the removable sections from the sheath 700. In some examples, the removal (e.g., tearing away) of the removable sections may allow the intermediate portion 626 to radially expand to axially contract the intermediate portion 626 to decrease the distance between the proximal portion 618 and the distal portion 620 to distance $D_2$, less than distance $D_1$. Additionally, turning to FIG. 7C, a physician may pull on the strings (e.g., strings 706C-706D) or otherwise manipulate the sheath 700 of the bridge device 600 to detach the removable sections (e.g., removable section 704C-704D) at the preferential tear line (e.g., preferential tear line 702C) and tear the removable sections from the sheath 700. In some examples, the removal (e.g., tearing away) of the removable sections may allow an additional portion of the intermediate portion 626 to radially expand to further axially contract the intermediate portion 626 to further decrease the distance between the proximal portion 618 and the distal portion 620 to distance $D_3$, less than distance $D_2$. Thus, with the proximal anchor 622 expanded in the disconnected proximal portion and the distal anchor 624 expanded in the disconnected distal portion of an esophagus, the distance between the proximal anchor 622 and the distal anchor 624 may be periodically reduced over the course of hours, days, or weeks by removing portions of the sheath 700 until the proximal anchor 622 has been moved toward the distal anchor 624 a sufficient amount to connect the two disconnected portions of the esophagus together.

Figure 8A:
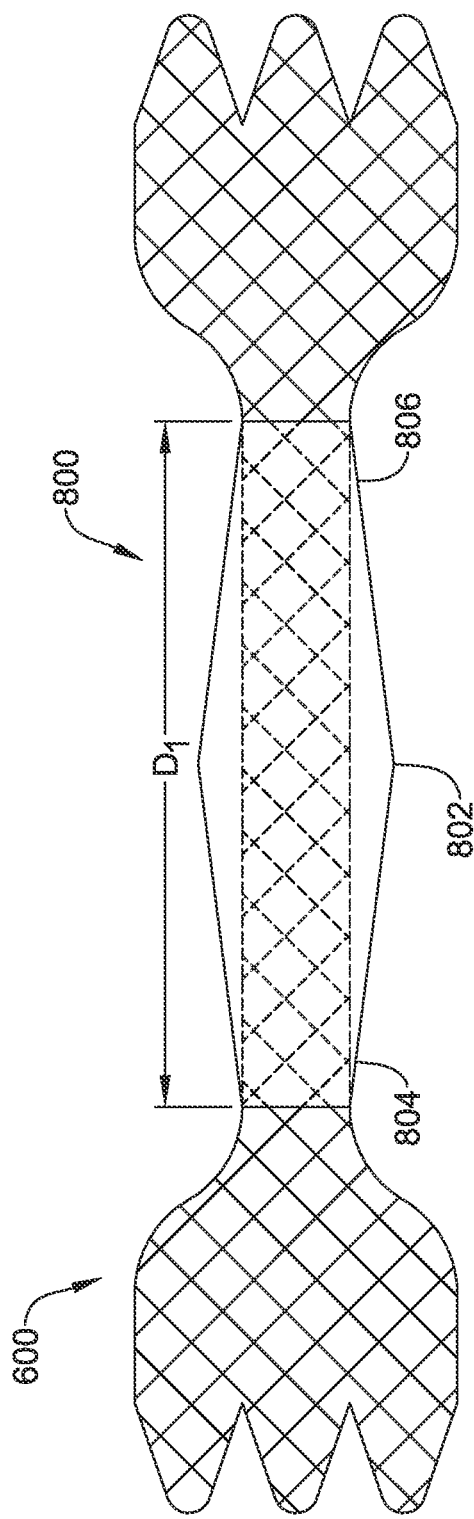
FIGS. 8A-8C illustrate another example of expansion of the intermediate portion of the esophageal atresia bridge device of FIG. 6 as a brace/link is removed.
Figure 8B:
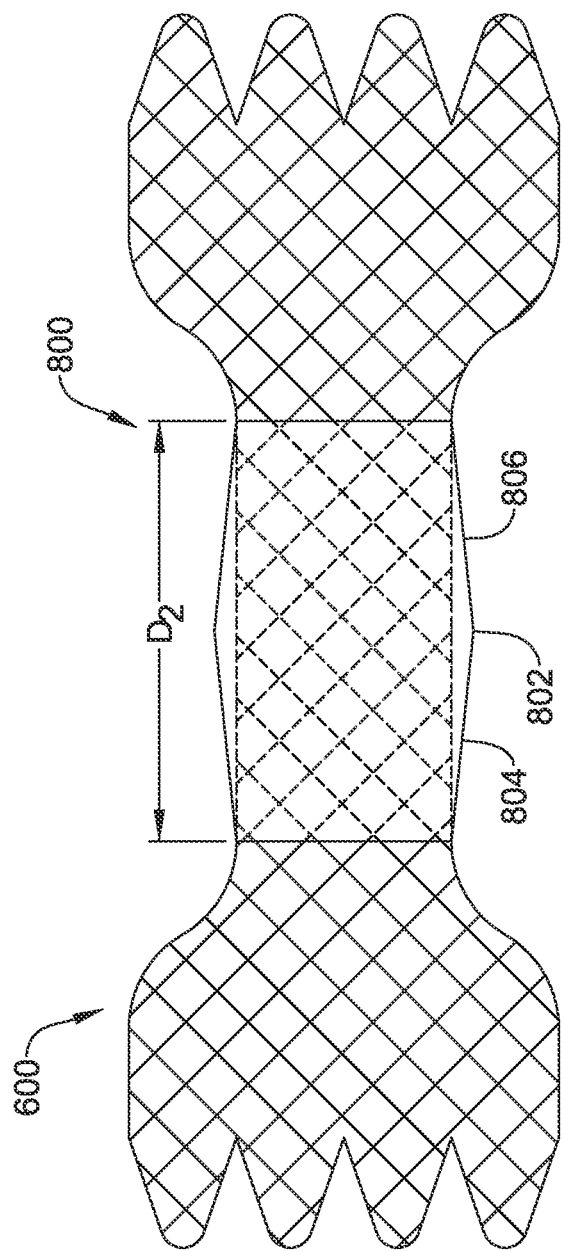
Figure 8C:
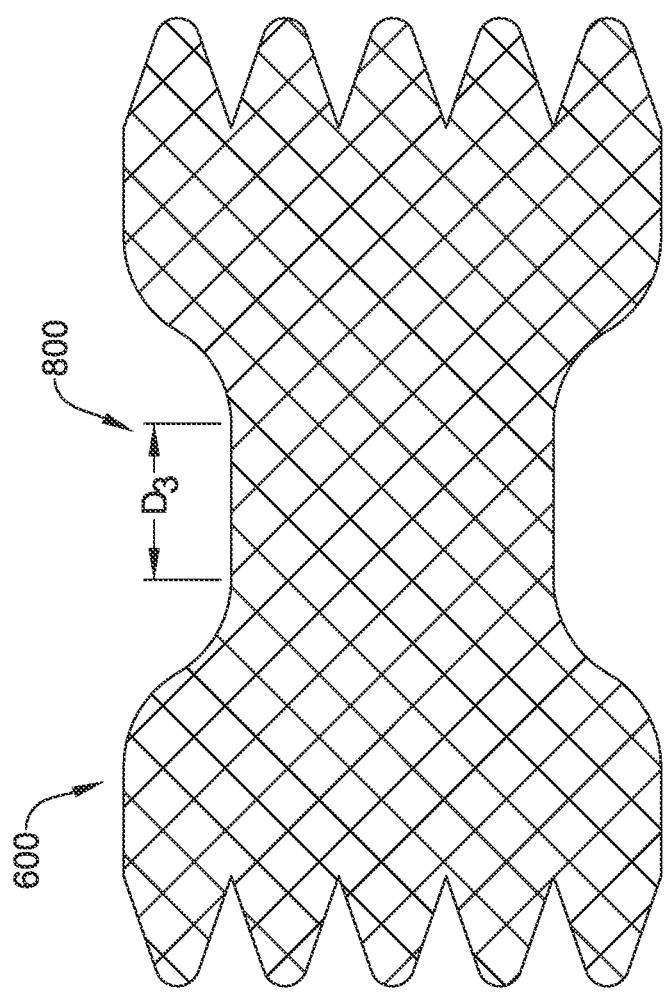

FIGS. 8A-8C illustrate another example of radial expansion and axial contraction of the intermediate portion 626 as a brace/link (e.g., sheath 800) is removed from the bridge device 600. The bridge device 600 includes a sheath 800 surrounding the intermediate portion 626 to radially constrain, and thus axially elongate the intermediate portion of the braided stent while the flanges of the braided stent, forming the proximal and distal anchors 622/624 are radially expanded. In some cases, the sheath 800 may be comprised of materials that allow the sheath 800 or portions thereof to degrade over time. In some instances, the sheath 800 may have areas of varying material, wall thickness, or strength across its length, so that certain portions of the sheath 800 may degrade faster than other portions, providing the sheath 800 with a progressively shorter length over a period of degradation. In the embodiment depicted in FIG. 8A, the sheath 800 has a varying rate of degradation along its length, which in the particular embodiment is achieved by varying a wall thickness along its length. In this case, an intermediate section 802 may have a greater wall thickness than at a proximal end 804 and distal end 806 of the sheath 800, respectively. Moreover, in some examples, the wall thickness of the sheath 800 may get progressively thinner moving away from the intermediate section 802 towards the proximal end 804 and distal end 806. In some cases, the thinner proximal end 804 and distal end 806 may fully degrade over time sooner than the intermediate section 802. As such, the thickened and stronger intermediate section 802 of the sheath 800 may resist radial expansion of the underlying intermediate portion of the stent longer than the portions of the intermediate portion of the stent underlying the proximal end 804 and distal end 806 of the sheath 800. As the portions of the intermediate portion of the stent are no longer radially constrained by the sheath 800, those portions of the intermediate portion of the stent are permitted to radially expand and thus axially contract to reduce the axial distance between the proximal anchor 622 and the distal anchor 624. This is just one example of how the sheath 800 may be configured to allow for a variation in the degradation rate of regions of the sheath 800.

In some examples, the wall thickness along the length of the sheath 800 may be relatively constant and the intermediate section 802 may be comprised of material that degrades slower than material comprising the proximal end 804 and distal end 806 of the sheath 800, providing the sheath 800 with a gradient of degradation along its length. Similarly, the proximal end 804 and distal end 806 may fully degrade over time sooner than the intermediate section 802, permitting controlled radially expansion of the underlying intermediate portion of the stent from the ends of the intermediate portion toward the central region of the intermediate portion. In some cases, a combination of material composition and varying wall thickness may be used to obtain controlled degradation of the sheath 800.

As shown in FIG. 8A, in some cases, the sheath 800 may be placed onto the intermediate portion 626 of the bridge device 600 (e.g., surround the intermediate portion of the braided stent, with the flared ends of the stent located on either end of the sheath 800 using methods known in the art. In some cases, the intermediate portion 626 may be restrained in a radially compressed configuration by the sheath 800. According to various embodiments, the sheath 800 may radially compress, and axially elongate the intermediate portion 626 such that the proximal portion 618 is an initial distance ($D_1$) from the distal portion 620. Turning to FIG. 8B, in some instances, the sheath 800, formed of a biodegradable material, may degrade over time. In this case, because the wall thickness is greater at the intermediate section 802 than the proximal end 804 and distal end 806, the proximal end 804 and distal end 806 may fully degrade before the intermediate section 802. In some examples, the degrading of the sheath 800 may allow the exposed portions of the intermediate portion 626 of the bridge device 600 to radially expand and axially contract to decrease the distance between the proximal portion 618 and the distal portion 620 to distance $D_2$, less than distance $D_1$. At this point, portions of the intermediate portion 626 still underlying the sheath 800 may remain held in a radially contracted state. Additionally, turning to FIG. 8C, the sheath 800 may continue to degrade over time from its ends toward the central region of the sheath 800. In this case, the sheath 800 may fully degrade over time allowing the intermediate portion 626 to further radially expand and axially contract to decrease the distance between the proximal portion 618 and the distal portion 620 to distance $D_3$, less than distance $D_2$.

Figure 9A:
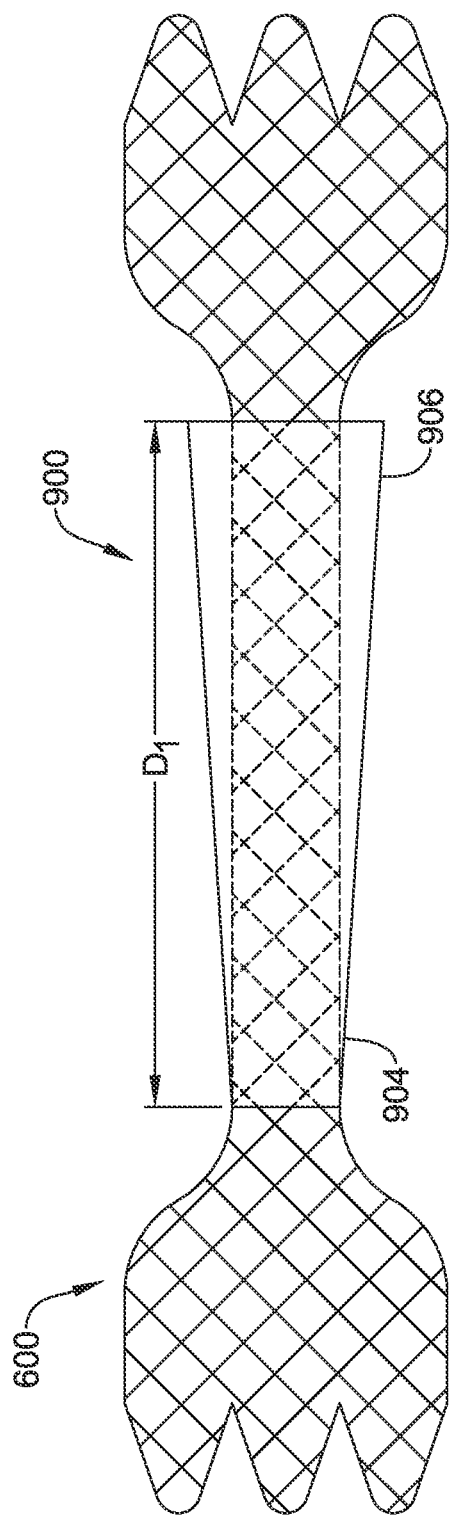
FIGS. 9A-9C illustrate another example of expansion of the intermediate portion of the esophageal atresia bridge device of FIG. 6 as a brace/link is removed.
Figure 9B:
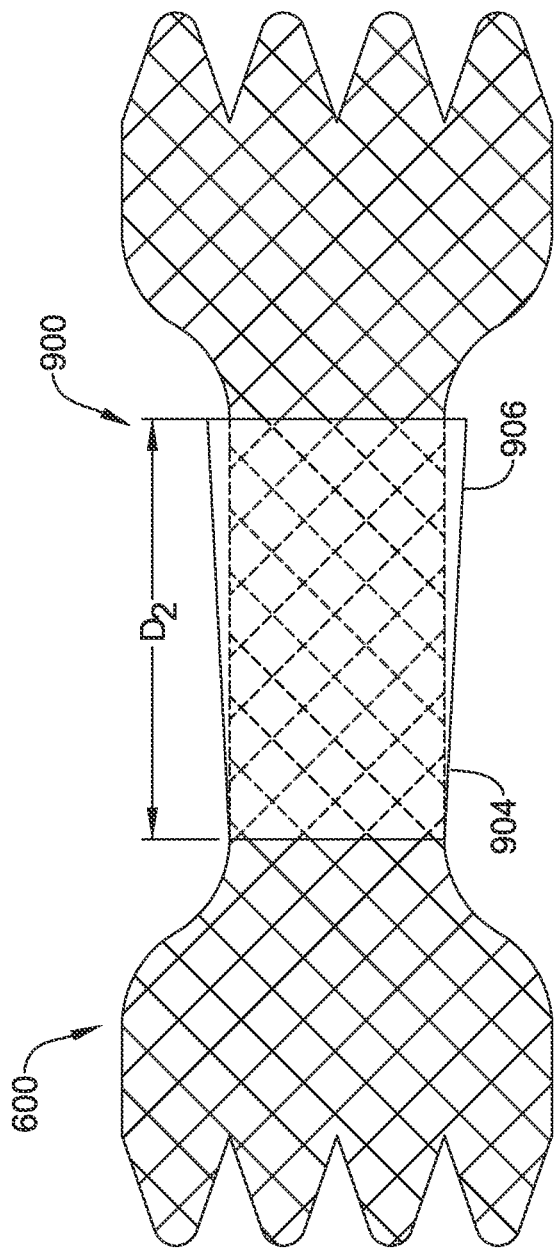
Figure 9C:
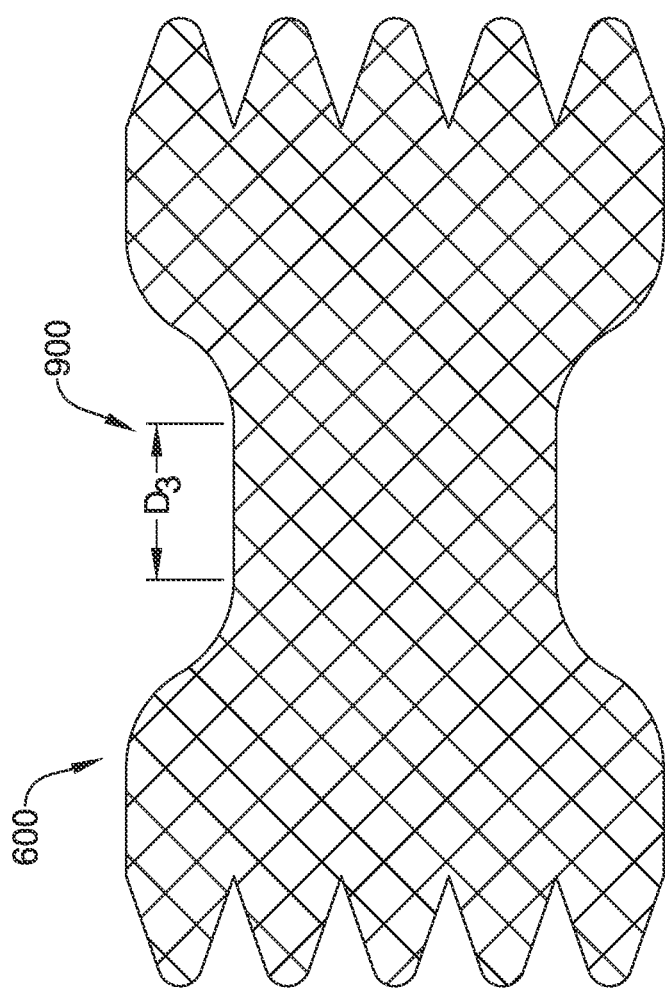

FIGS. 9A-9C illustrate another example of radial expansion and axial contraction of the intermediate portion 626 as a brace/link (e.g., sheath 900) is removed from the bridge device 600. The bridge device 600 includes a sheath 900 surrounding the intermediate portion 626 to radially constrain, and thus axially elongate the intermediate portion of the braided stent while the flanges of the braided stent, forming the proximal and distal anchors 622/624 are radially expanded. Similar to sheath 800, the sheath 900 may be comprised of materials that allow the sheath 900 or portions thereof to degrade over time. In some instances, the sheath 900 may have areas of varying material, wall thickness, or strength across its length, so that certain portions of the sheath 900 will degrade faster than other portions, providing the sheath 900 with a progressively shorter length over a period of degradation. In the embodiment depicted in FIG. 9A, the sheath 900 has a varying rate of degradation along its length, which in the particular embodiment is achieved by varying a wall thickness along its length. In this case, a first end, such as distal end 906, may have a greater wall thickness than a second end, such as proximal end 904, of the sheath 900, respectively. Moreover, in some examples, the wall thickness of the sheath 900 may get progressively thicker away from the proximal end 904 toward the distal end 906. However, in other instances, the wall thickness of the sheath 900 may get progressively thicker away from the distal end 906 toward the proximal end 904, for example. In some cases, the portion of the sheath 900 having a thinner wall thickness may fully degrade faster than portions of the sheath 900 with a thicker wall thickness. For example, the thinner proximal end 904 may fully degrade over time sooner than the distal end 906. As such, the thickened and stronger distal end 906 of the sheath 900 may resist radial expansion of the underlying distal portion of the stent longer than the portions of the intermediate portion of the stent underlying the proximal end 904 of the sheath 900. As the portions of the intermediate portion of the stent are no longer radially constrained by the sheath 900, those portions of the intermediate portion of the stent are permitted to radially expand and thus axially contract to reduce the axial distance between the proximal anchor 622 and the distal anchor 624. As shown in FIG. 9A, in some cases, the sheath 900 may be placed onto the intermediate portion 626 of the bridge device 600 (e.g., surround the intermediate portion of the braided stent, with the flared ends of the stent located on either end of the sheath 900 using methods known in the art. In some cases, the intermediate portion 626 may be restrained in a radially compressed configuration by the sheath 900. According to various embodiments, the sheath 900 may radially compress, and axially elongate the intermediate portion 626 such that the proximal portion 618 is an initial distance ($D_1$) from the distal portion 620. Turning to FIG. 9B, in some instances, the sheath 900, formed of a biodegradable material, may degrade over time. In this case, because the wall thickness is greater at the distal end 906 than the proximal end 904, the proximal end 904 may fully degrade before the distal end 906. In some examples, the degrading of the sheath 900 may allow the exposed portions of the intermediate portion 626 of the bridge device 600 to radially expand and axially contract to decrease the distance between the proximal portion 618 and the distal portion 620 to distance $D_2$, less than distance $D_1$. At this point, portions of the intermediate portion 626 still underlying the sheath 900 may remain held in a radially contracted state. Additionally, turning to FIG. 9C, the sheath 900 may continue to degrade over time from one end to the other end. In this case, the sheath 900 may fully degrade over time allowing the intermediate portion 626 to further radially expand and axially contract to decrease the distance between the proximal portion 618 and the distal portion 620 to distance $D_3$, less than distance $D_2$.

Figure 10A:
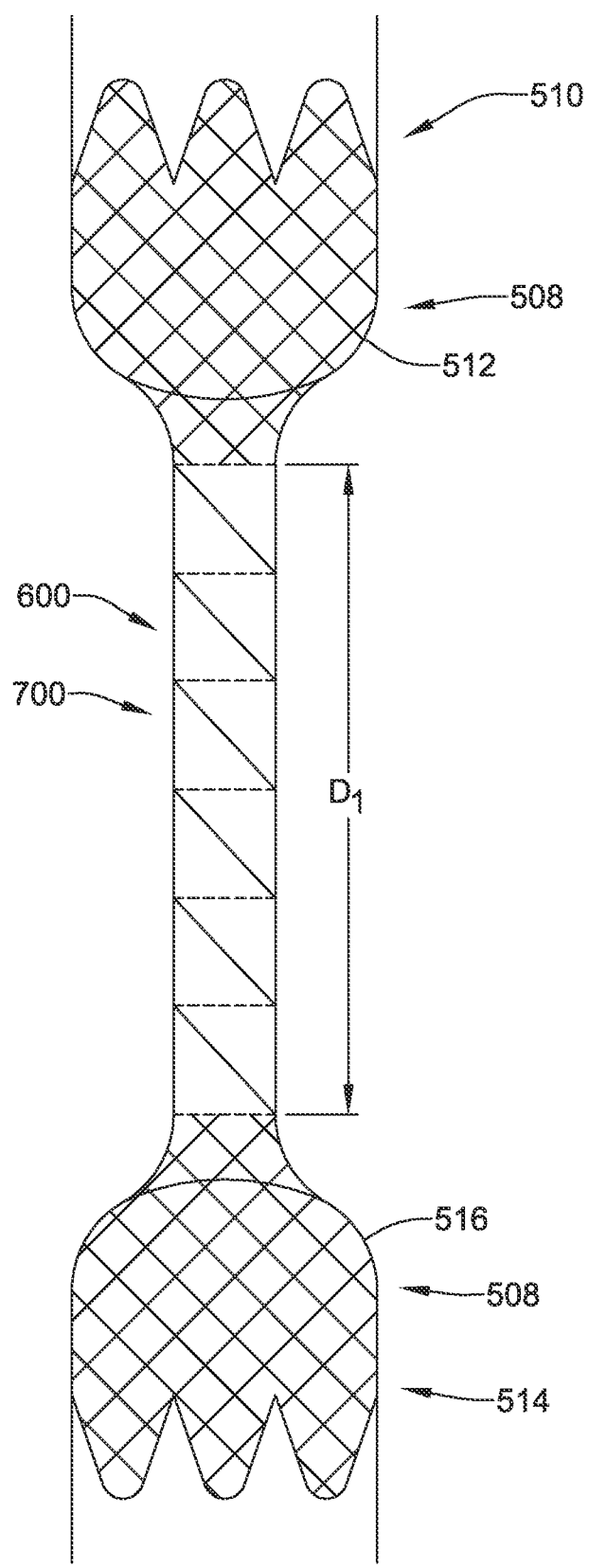
FIGS. 10A-10D show access to and implantation of the esophageal atresia bridge device of FIG. 6 and the brace/link of FIGS. 7A-7C.
Figure 10B:
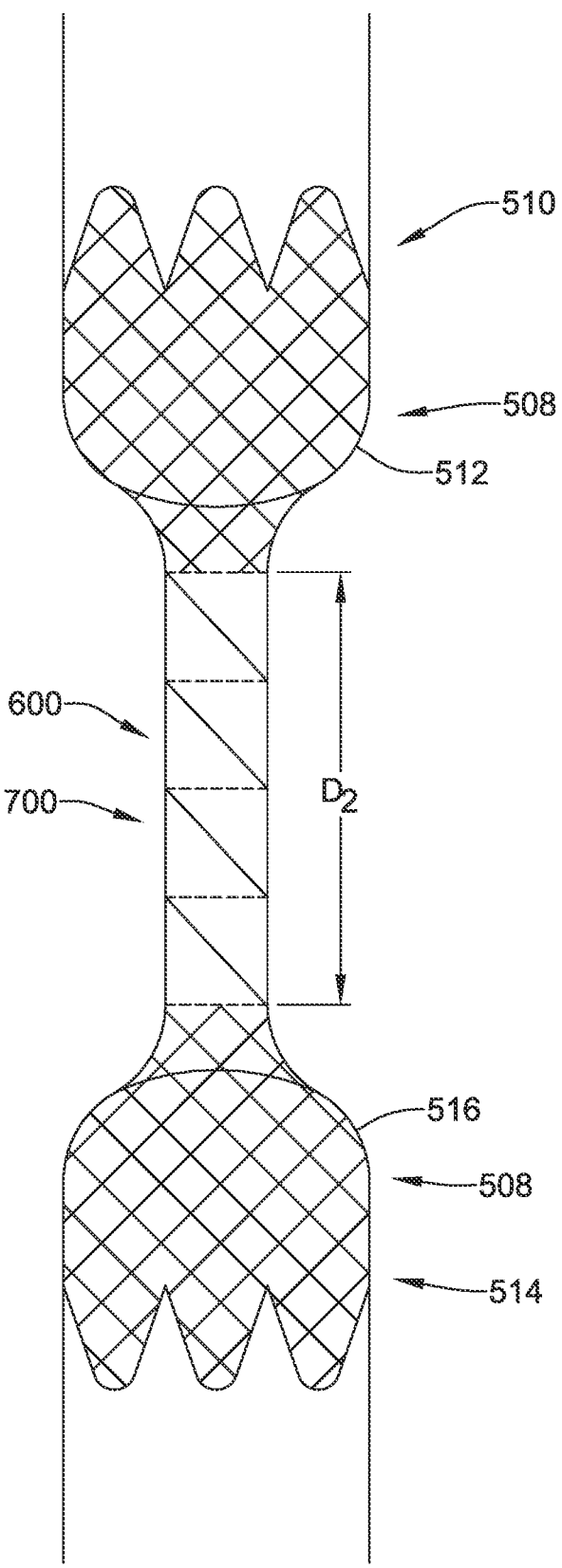
Figure 10C:
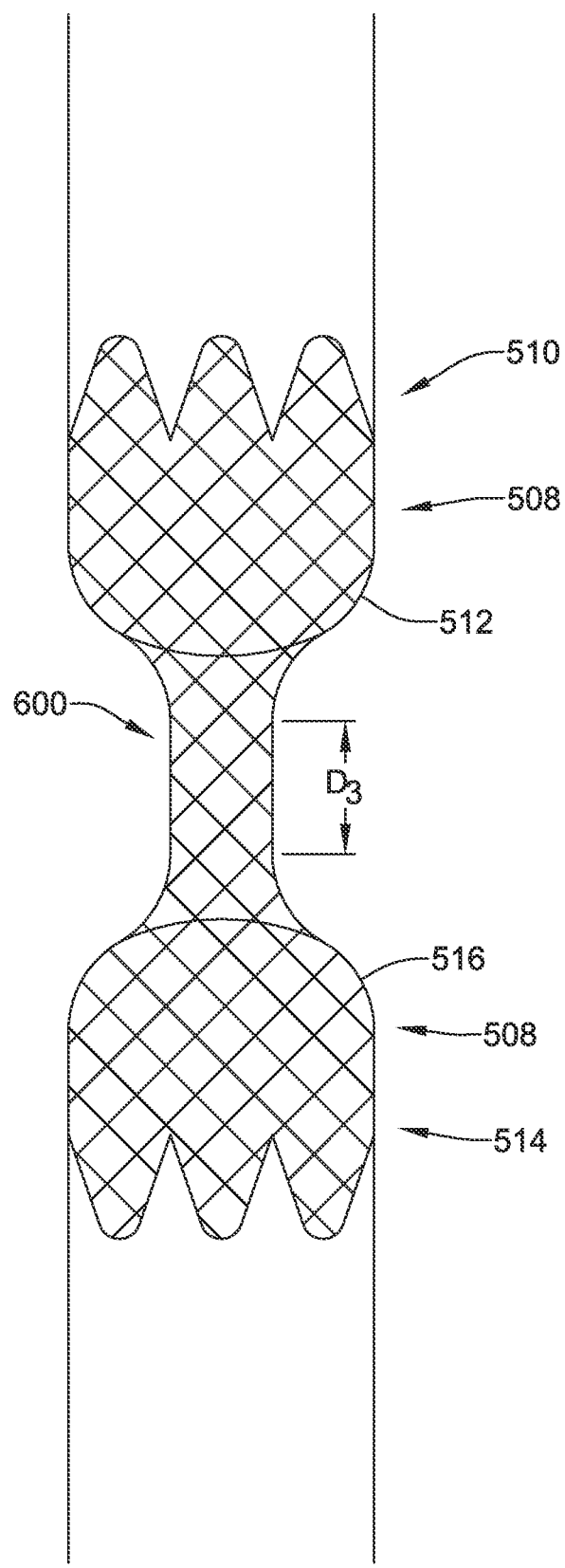

FIGS. 10A-10D show access to and implantation of the esophageal atresia bridge device 600 and sheath 700. Although the bridge device 600 is depicted with the sheath 700, it is noted that the sheath 700 may be substituted with another other desired sheath disclosed herein, if desired. Typically, a stent may be delivered by a deployment system or "introducer" (not shown) to the site where it is required. The introducer may enter the body through the patient's mouth using standard access techniques know in the art. In another technique, the stomach may be punctured with a hollow needle or trocar, for example under ultrasound guidance, to gain access to the patient's stomach. In this example, the introducer may be advanced to the end 512 of the proximal section 510 of the esophagus 508. The introducer may then be further advanced to extend from the proximal section 510 to the end 516 of the distal section 514 of the esophagus 508. In some cases, the introducer may be configured to penetrate through the end 512 of the proximal section 510 and the end 516 of the distal section 514 of the esophagus 508, such that the introducer passes into the distal section 514 of the esophagus 508. The introducer may then be manipulated to cause the bridge device 600 and sheath 700 to be released or deployed from the introducer. As shown in FIG. 10A, the proximal portion 618 may be an initial distance ($D_1$) from the distal portion 620. In some cases, the proximal anchor 622 may be configured to expand to push against and engage the tissue of a luminal wall of the proximal section 510 of the esophagus 508 near the end 512 of the proximal section 510 to anchor the bridge device 600 to the proximal section 510 of the esophagus 508. Similarly, the distal anchor 624 may be configured to expand to push against and engage the tissue of a luminal wall of the distal section 514 of the esophagus 508 near the end 516 of the distal section 514 to anchor the bridge device 600 to the distal section 514 of the esophagus 508. The intermediate portion 626 may extend between the proximal section 510 and the distal section 514 of the esophagus 508. In some instances, in this position, the bridge device 600 may apply a controlled tension that pulls the proximal section 510 of the esophagus 508 towards the distal section 514 of the esophagus 508 and stretch the esophagus over time. Turning to FIG. 10B, after the esophagus has had time to stretch, the strings may be pulled to incrementally detach the removable sections of the sheath 700 at the preferential tear lines and tear the removable sections from the sheath 700. In some examples, the tearing away of the removable sections may allow the intermediate portion 626 to radially expand and axially contract, thus moving the proximal anchor 622 toward the distal anchor 624 to decrease the distance between the proximal portion 618 and the distal portion 620 to distance $D_2$. Accordingly, the bridge device 600 may again apply a controlled tension that pulls and stretches the proximal section 510 of the esophagus 508 further towards the distal section 514 of the esophagus 508. Similarly, turning to FIG. 10C, after the esophagus has had time to stretch, the strings may be further pulled to detach the removable sections at the preferential tear lines and tear the additional removable sections from the sheath 700. In some examples, the tearing away of the removable sections may allow the intermediate portion 626 to further radially expand and axially contract, thus moving the proximal anchor 622 further toward the distal anchor 624 to further decrease the distance between the proximal portion 618 and the distal portion 620 to distance $D_3$.

Figure 10D:
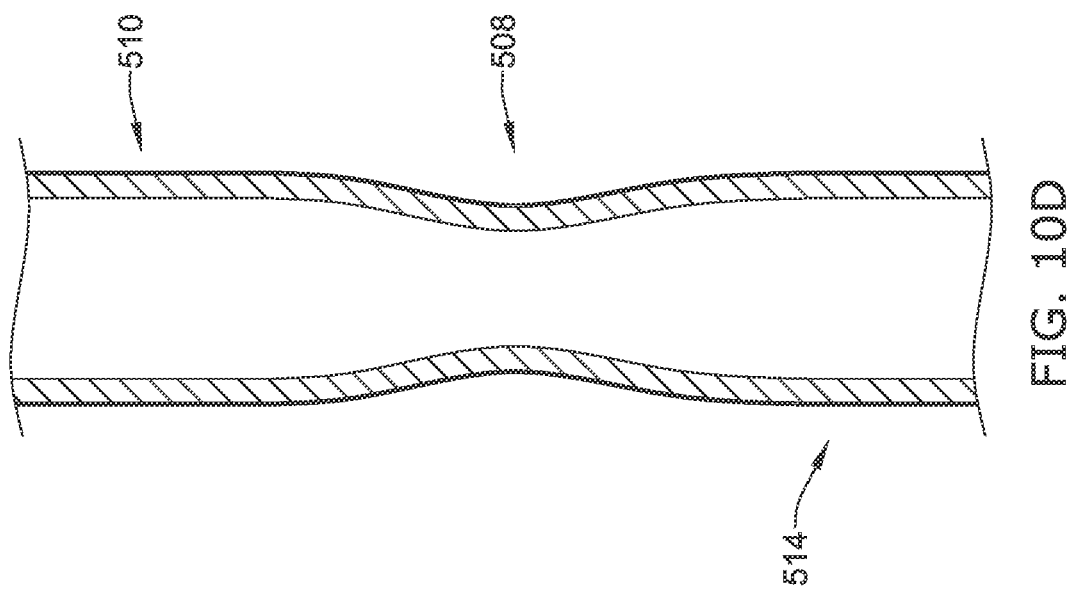

Turning to FIG. 10D, when the proximal section 510 is close enough to the distal section 514 of the esophagus 508 the bridge device 600 may be removed and the disconnected portions of the esophagus may be connected. Accordingly, the proximal section 510 may be connected to the distal section 514, such as with sutures (i.e., the proximal section 510 and/or the distal section 514 have been stretched enough such that any tension administered to connect the proximal section to the distal section will not cause unwanted tearing of the tissue of the proximal section or the distal section).

Figure 11A:
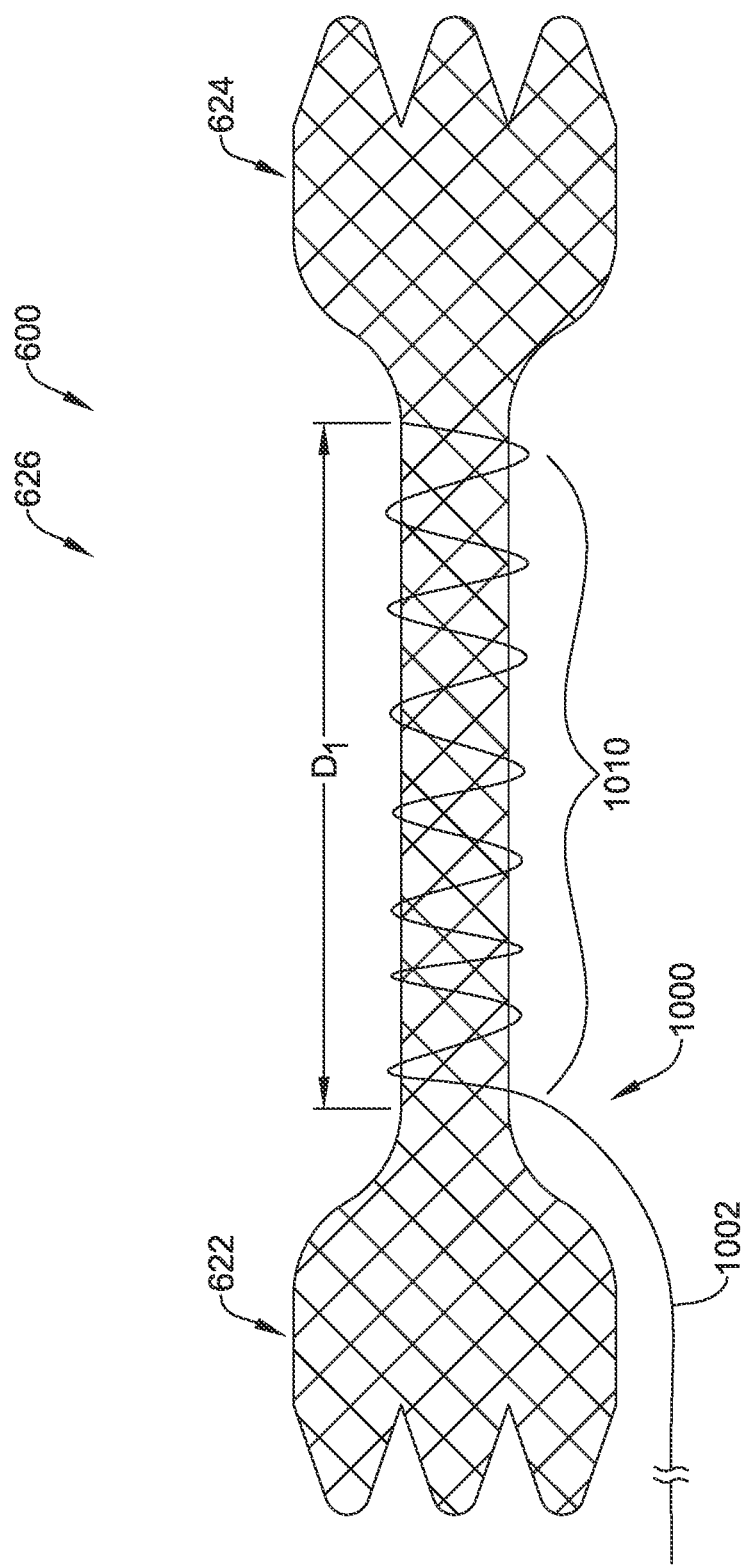
FIGS. 11A-11C illustrate another example of expansion of the intermediate portion of the esophageal atresia bridge device of FIG. 6 as a brace/link is removed.
Figure 11B:
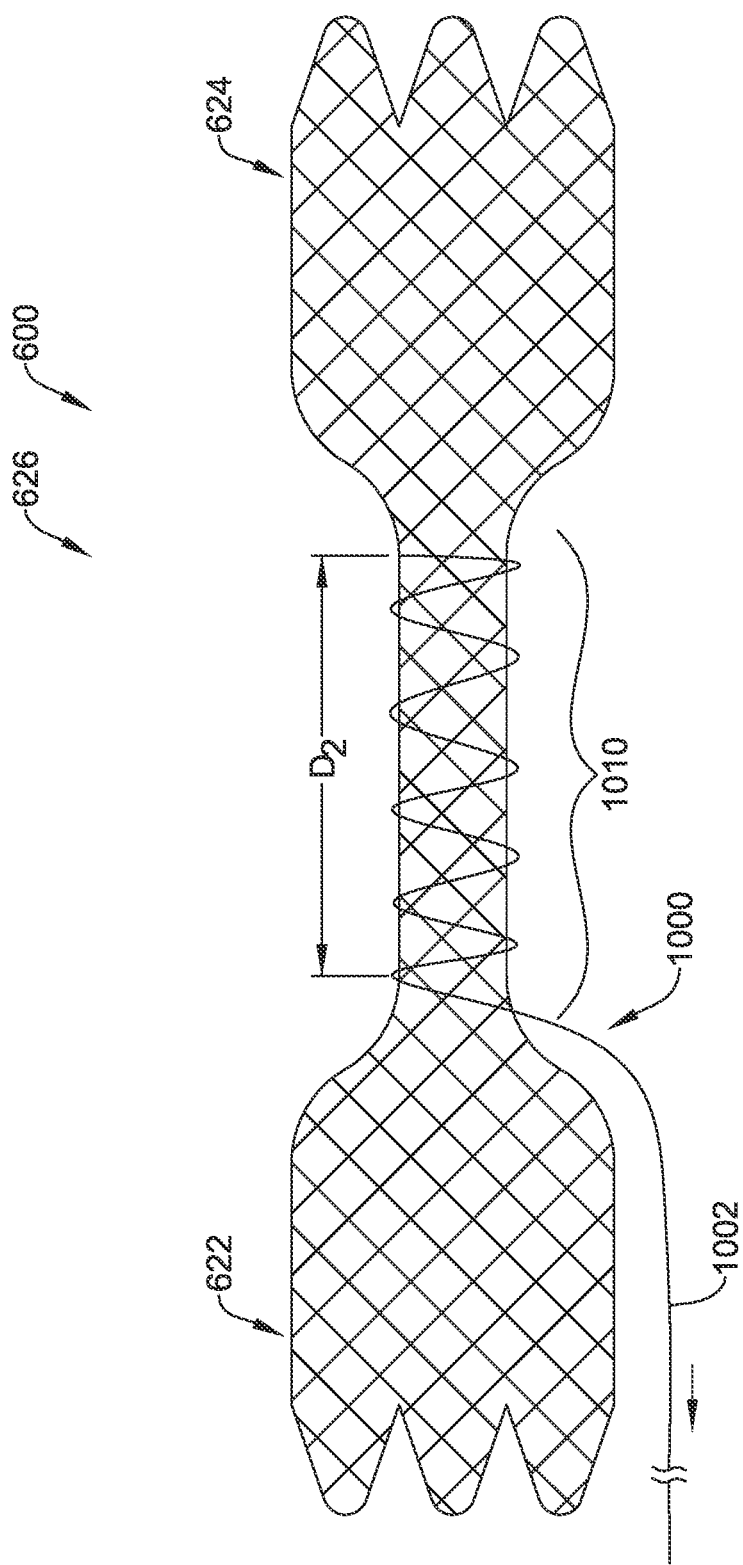
Figure 11C:
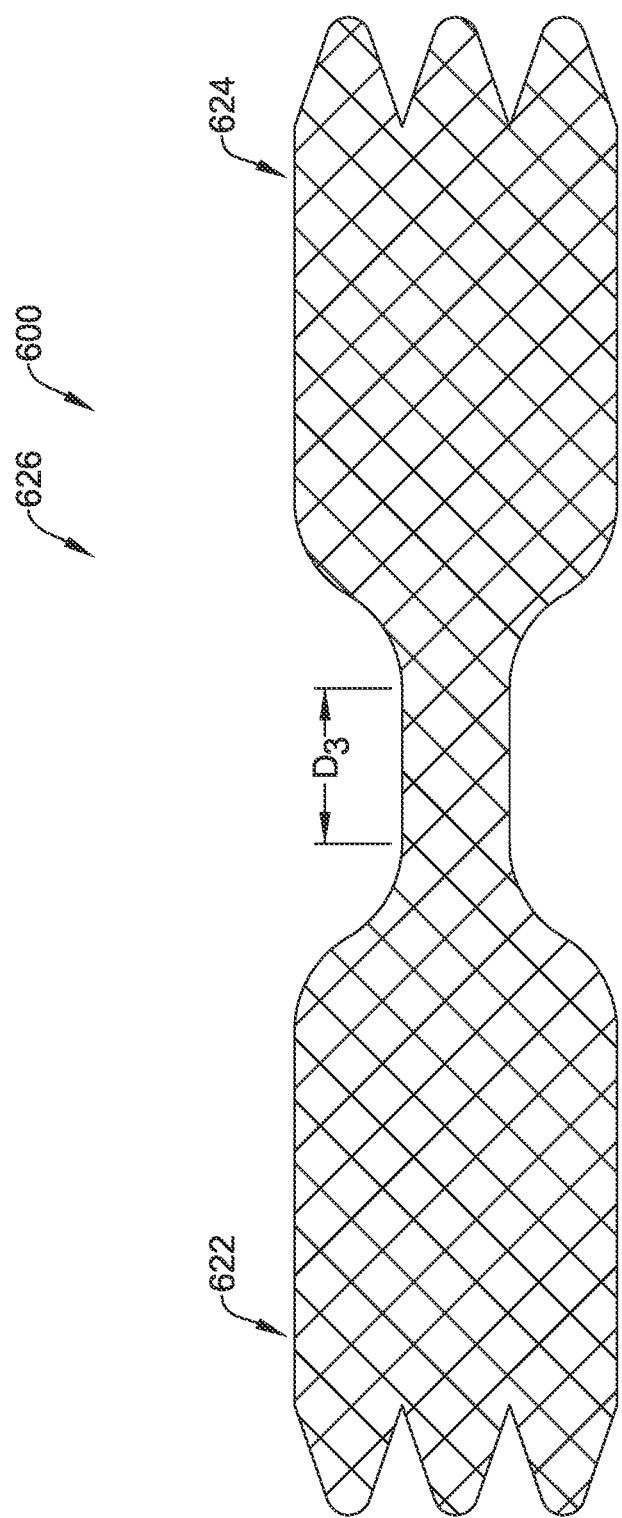

FIGS. 11A-11C illustrate another example of radial expansion and axial contraction of the intermediate portion 626 as a brace/link (e.g., sheath 1000) is removed from the bridge device 600. The bridge device 600 includes a sheath 1000 surrounding the intermediate portion 626 to radially constrain, and thus axially elongate the intermediate portion of the braided stent while the flanges of the braided stent, forming the proximal and distal anchors 622/624 are radially expanded. The sheath 1000 may comprise a filament 1002 having a crocheted or knotted portion 1010 surrounding the intermediate portion 626 and an end portion extending from the stent to be manipulated from exterior of the patient. In the embodiment depicted in FIG. 11A, the crocheted portion of sheath 1000 surrounding the intermediate portion 626 prevents radial expansion of the underlying intermediate portion. In some cases, the intermediate portion 626 may be restrained in a radially compressed configuration by the sheath 1000.

As shown in FIG. 11B, the filament 1002 may be pulled to sequentially unravel a portion of the filament and/or release a knot to allow a portion of the stent that is no longer constrained by the filament 1002 to radially expand and axially contract. As the portions of the intermediate portion of the stent are no longer radially constrained by the filament 1002, those portions of the intermediate portion of the stent are permitted to radially expand and thus axially contract to reduce the axial distance between the proximal anchor 622 and the distal anchor 624. In some examples, unraveling or untying a portion of the length of the filament 1002 may allow the exposed portions of the intermediate portion 626 of the bridge device 600 to radially expand and axially contract to decrease the distance between the proximal portion 618 and the distal portion 620 to distance $D_2$, less than distance $D_1$. At this point, portions of the intermediate portion 626 still underlying the sheath 1000 may remain held in a radially contracted state. Additionally, turning to FIG. 11C, the filament 1002 of the sheath 1000 may continue to be unraveled or untied over time to completely release the intermediate portion 626. In this case, the sheath 1000 may be fully unraveled or untied over time allowing the intermediate portion 626 to further radially expand and axially contract to decrease the distance between the proximal portion 618 and the distal portion 620 to distance $D_3$, less than distance $D_2$. Thus, with the proximal anchor 622 expanded in the disconnected proximal portion and the distal anchor 624 expanded in the disconnected distal portion of an esophagus, the distance between the proximal anchor 622 and the distal anchor 624 may be periodically reduced over the course of hours, days, or weeks by unraveling or untying portions of the filament 1002 of the sheath 1000 surrounding the intermediate portion 626 until the proximal anchor 622 has been moved toward the distal anchor 624 a sufficient amount to connect the two disconnected portions of the esophagus together.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of treating esophageal atresia, comprising:
   inserting an elongate member of an esophageal atresia device into a mouth of a patient, the esophageal atresia device including a rotatable member including a threaded region; and
   rotating the rotatable member relative to the elongate member, wherein rotation of the rotatable member relative to the elongate member causes longitudinal movement of the distal end of the elongate member relative to the rotatable member in order to apply a force to a proximal pouch of the patient's esophagus.

2. The method of claim 1, wherein the elongate member includes a threaded region threadably engaging the threaded region of the rotatable member.

3. The method of claim 2, wherein the threaded region of the elongate member extends distally from the rotatable member.

4. The method of claim 3, wherein the rotatable member includes a threaded lumen including the threaded region of the rotatable member, wherein the threaded region of the elongate member extends into the threaded lumen.

5. The method of claim 1, wherein the force applied to the proximal pouch draws the proximal pouch closer to a distal pouch of the patient's esophagus over time.

6. The method of claim 5, further comprising, surgically attaching the proximal pouch to the distal pouch.

7. The method of claim 1, wherein the elongate member includes an enlarged portion for engaging the proximal pouch.

8. The method of claim 1, wherein the rotatable member includes a radially extending flange coupled thereto.

9. The method of claim 8, wherein the radially extending flange is rotatable relative to the rotatable member.

10. The method of claim 1, wherein the elongate member applies a force to a distal pouch of the patient's esophagus.

11. A method of treating esophageal atresia, comprising:
inserting an elongate member of an esophageal atresia device into a mouth of a patient, the esophageal atresia device including a rotatable member including a threaded region;
applying a force to a proximal pouch of the patient's esophagus with a portion of the esophageal atresia device; and
rotating the rotatable member relative to the elongate member, wherein rotation of the rotatable member relative to the elongate member increases the force applied to the proximal pouch of the patient's esophagus by the portion of the esophageal atresia device.

12. The method of claim 11, wherein the elongate member includes a threaded region threadably engaging the threaded region of the rotatable member.

13. The method of claim 12, wherein the threaded region of the elongate member extends distally from the rotatable member.

14. The method of claim 13, wherein the rotatable member includes a threaded lumen including the threaded region of the rotatable member, wherein the threaded region of the elongate member extends into the threaded lumen.

15. The method of claim 11, wherein the force applied to the proximal pouch draws the proximal pouch closer to a distal pouch of the patient's esophagus over time.

16. The method of claim 15, further comprising, surgically attaching the proximal pouch to the distal pouch.

17. A method of treating esophageal atresia, comprising:
inserting an elongate member of an esophageal atresia device into a mouth of a patient, the esophageal atresia device including a rotatable member including a threaded region; and
drawing a proximal pouch of the patient's esophagus closer to a distal pouch of the patient's esophagus via rotation of the rotatable member relative to the elongate member;
wherein the elongate member includes a threaded region threadably engaging the threaded region of the rotatable member.

18. The method of claim 17, wherein the threaded region of the elongate member extends distally from the rotatable member.

19. The method of claim 18, wherein the rotatable member includes a threaded lumen including the threaded region of the rotatable member, wherein the threaded region of the elongate member extends into the threaded lumen.

* * * * *